US008124405B2

(12) United States Patent
Foster et al.

(10) Patent No.: US 8,124,405 B2
(45) Date of Patent: *Feb. 28, 2012

(54) FUSION PROTEINS

(75) Inventors: Keith Alan Foster, Salisbury (GB); John Chaddock, Salisbury (GB); Philip Marks, Salisbury (GB); Patrick Stancombe, Salisbury (GB); Lyndsey Durose, Salisbury (GB)

(73) Assignee: Syntaxin Limited, Abingdon, Oxfordshire (GB)

( * ) Notice: Subject to any disclaimer, the term of this patent is extended or adjusted under 35 U.S.C. 154(b) by 454 days.

This patent is subject to a terminal disclaimer.

(21) Appl. No.: 11/853,517

(22) Filed: Sep. 11, 2007

(65) Prior Publication Data

US 2008/0064092 A1    Mar. 13, 2008

Related U.S. Application Data

(63) Continuation of application No. 11/792,076, filed as application No. PCT/GB2005/004606 on Dec. 1, 2005.

(30) Foreign Application Priority Data

Dec. 1, 2004    (GB) .................................. 0426397.6

(51) Int. Cl.
  *C07K 14/00*    (2006.01)
  *C12N 15/62*    (2006.01)
  *C12N 15/63*    (2006.01)

(52) U.S. Cl. ..................... 435/320.1; 530/350; 536/23.4

(58) Field of Classification Search ......................... None
  See application file for complete search history.

(56) References Cited

U.S. PATENT DOCUMENTS

| 7,811,584 B2 * | 10/2010 | Steward et al. ............ 424/239.1 |
| 2003/0166238 A1 * | 9/2003 | Shone et al. .................. 435/219 |
| 2008/0213830 A1 * | 9/2008 | Steward et al. .............. 435/69.1 |

FOREIGN PATENT DOCUMENTS

| WO | WO 98/07864 | 2/1998 |
| WO | WO 01/14570 A1 | 3/2001 |
| WO | WO 01/21213 A3 | 3/2001 |
| WO | WO 01/62269 | 8/2001 |
| WO | WO 02/074327 A3 | 9/2002 |
| WO | WO 2004/024909 A2 | 3/2004 |

OTHER PUBLICATIONS

J. M. Sutton, et al., "Preparation of Specifically Activatable Endopeptidase Derivatives of *Clostridium botulinum* Toxins Type A, B and C and their Applications," Protein Expression and Purification, Academic Press, vol. 40, No. 1, Mar. 2005, pp. 31-41.
J. A. Chaddock, et al., "Clostridial Neurotoxins: Structure-function Led Design of New Therapeutics," Cellular and Molecular Life Sciences: CMLS, vol. 63, No. 5, Mar. 2006, pp. 540-551.
Michaela Robbie-Ryan, "The role of mast cells in allergy and autoimmunity" ScienceDirect, Current Opinion in Immunology, vol. 14, Issue 6, Dec. 1, 2002.
David A. Brenner, "Prolonged activation of jun and collagenase genes by tumour necrosis factor" Letters to Nature, 337, Feb. 16, 1989.
Stack Wa, "Randomized controlled trial of CDP571 antibody to tumour necrosis factor-alpha in Crohn's disease" PubMed, Lancet, Feb. 22, 1997; 349(9051).
C. Parkinson, "The relationship between Serum GH and Serum IGF-I in Acromegaly is Gender-Specific" The Journal of Clinical Endocrinology & Metabolism, Metabolism 86(11); p. 5240; [2001].
Ira D. Goldfine, "Medical Treatment of Acromegaly" Ann. Rev. Med. [1978] 29; p. 407.
Foster, Keith A. "The Analgesic Potential of Clostridial Neurotoxin Derivatives" Expert Opinion, Ashley Publications, (2004) 13(11); pp. 1437-1443.

* cited by examiner

*Primary Examiner* — Scott Long
(74) *Attorney, Agent, or Firm* — Morris, Manning & Martin, LLP; Christopher W. Raimund

(57) ABSTRACT

The invention provides a single chain, polypeptide fusion protein, comprising: a non-cytotoxic protease, or a fragment thereof, which protease or protease fragment is capable of cleaving a protein of the exocytic fusion apparatus of a target cell; a Targeting Moiety that is capable of binding to a Binding Site on the target cell, which Binding Site is capable of undergoing endocytosis to be incorporated into an endosome within the target cell; a protease cleavage site at which site the fusion protein is cleavable by a protease, wherein the protease cleavage site is located between the non-cytotoxic protease or fragment thereof and the Targeting Moiety; and a translocation domain that is capable of translocating the protease or protease fragment from within an endosome, across the endosomal membrane and into the cytosol of the target cell.

7 Claims, 1 Drawing Sheet

FUSION PROTEINS

CROSS REFERENCE TO RELATED APPLICATIONS

This application is a continuation of U.S. patent application Ser. No. 11/792,076, filed Jun. 1, 2007, pending, which is a national phase entry of International Application No. PCT/GB2005/04606, filed Dec. 1, 2005. Each of the above applications is hereby incorporated by reference in its entirety.

This invention relates to non-cytotoxic fusion proteins, and to the therapeutic application thereof.

Toxins may be generally divided into two groups according to the type of effect that they have on a target cell. In more detail, the first group of toxins kill their natural target cells, and are therefore known as cytotoxic toxin molecules. This group of toxins is exemplified inter alia by plant toxins such as ricin, and abrin, and by bacterial toxins such as diphtheria toxin, and Pseudomonas exotoxin A. Cytotoxic toxins have attracted much interest in the design of "magic bullets" (eg. immunoconjugates, which comprise a cytotoxic toxin component and an antibody that binds to a specific marker on a target cell) for the treatment of cellular disorders and conditions such as cancer. Cytotoxic toxins typically kill their target cells by inhibiting the cellular process of protein synthesis.

The second group of toxins, which are known as non-cytotoxic toxins, do not (as their name confirms) kill their natural target cells. Non-cytotoxic toxins have attracted much less commercial interest than have their cytotoxic counterparts, and exert their effects on a target cell by inhibiting cellular processes other than protein synthesis. Non-cytotoxic toxins are produced by a variety of plants, and by a variety of microorganisms such as *Clostridium* sp. and *Neisseria* sp.

Clostridial neurotoxins are proteins that typically have a molecular mass of the order of 150 kDa. They are produced by various species of bacteria, especially of the genus *Clostridium*, most importantly *C. tetani* and several strains of *C. botulinum, C. butyricum* and *C. argentinense*. There are at present eight different classes of the clostridial neurotoxin, namely: tetanus toxin, and botulinum neurotoxin in its serotypes A, B, C1, D, E, F and G, and they all share similar structures and modes of action.

Clostridial neurotoxins represent a major group of non-cytotoxic toxin molecules, and are synthesised by the host bacterium as single polypeptides that are modified post-translationally by a proteolytic cleavage event to form two polypeptide chains joined together by a disulphide bond. The two chains are termed the heavy chain (H-chain), which has a molecular mass of approximately 100 kDa, and the light chain (L-chain), which has a molecular mass of approximately 50 kDa.

L-chains possess a protease function (zinc-dependent endopeptidase activity) and exhibit a high substrate specificity for vesicle and/or plasma membrane associated proteins involved in the exocytic process. L-chains from different clostridial species or serotypes may hydrolyse different but specific peptide bonds in one of three substrate proteins, namely synaptobrevin, syntaxin or SNAP-25. These substrates are important components of the neurosecretory machinery.

*Neisseria* sp., most importantly from the species *N. gonorrhoeae*, produce functionally similar non-cytotoxic proteases. An example of such a protease is IgA protease (see WO99/58571).

It has been well documented in the art that toxin molecules may be re-targeted to a cell that is not the toxin's natural target cell. When so re-targeted, the modified toxin is capable of binding to a desired target cell and, following subsequent translocation into the cytosol, is capable of exerting its effect on the target cell. Said re-targeting is achieved by replacing the natural Targeting Moiety (TM) of the toxin with a different TM. In this regard, the TM is selected so that it will bind to a desired target cell, and allow subsequent passage of the modified toxin into an endosome within the target cell. The modified toxin also comprises a translocation domain to enable entry of the non-cytotoxic protease into the cell cytosol. The translocation domain can be the natural translocation domain of the toxin or it can be a different translocation domain obtained from a microbial protein with translocation activity.

For example, WO94/21300 describes modified clostridial neurotoxin molecules that are capable of regulating Integral Membrane Protein (IMP) density present at the cell surface of the target cell. The modified neurotoxin molecules are thus capable of controlling cell activity (eg. glucose uptake) of the target cell. WO96/33273 and WO99/17806 describe modified clostridial neurotoxin molecules that target peripheral sensory afferents. The modified neurotoxin molecules are thus capable of demonstrating an analgesic effect. WO00/10598 describes the preparation of modified clostridial neurotoxin molecules that target mucus hypersecreting cells (or neuronal cells controlling said mucus hypersecreting cells), which modified neurotoxins are capable of inhibiting hypersecretion from said cells. WO01/21213 describes modified clostridial neurotoxin molecules that target a wide range of different types of non-neuronal target cells. The modified molecules are thus capable of preventing secretion from the target cells. Additional publications in the technical field of re-targeted toxin molecules include:—WO00/62814; WO00/04926; U.S. Pat. No. 5,773,586; WO93/15766; WO00/61192; and WO99/58571.

The above-mentioned TM replacement may be effected by conventional chemical conjugation techniques, which are well known to a skilled person. In this regard, reference is made to Hermanson, G. T. (1996), Bioconjugate techniques, Academic Press, and to Wong, S. S. (1991), Chemistry of protein conjugation and cross-linking, CRC Press.

Chemical conjugation is, however, often imprecise. For example, following conjugation, a TM may become joined to the remainder of the conjugate at more than one attachment site.

Chemical conjugation is also difficult to control. For example, a TM may become joined to the remainder of the modified toxin at an attachment site on the protease component and/or on the translocation component. This is problematic when attachment to only one of said components (preferably at a single site) is desired for therapeutic efficacy.

Thus, chemical conjugation results in a mixed population of modified toxin molecules, which is undesirable.

As an alternative to chemical conjugation, TM replacement may be effected by recombinant preparation of a single polypeptide fusion protein (see WO98/07864). This technique is based on the in vivo bacterial mechanism by which native clostridial neurotoxin (ie. holotoxin) is prepared, and results in a fusion protein having the following structural arrangement:

$NH_2$-[protease component]-[translocation component]-[TM]-COOH

According to WO98/07864, the TM is placed towards the C-terminal end of the fusion protein. The fusion protein is then activated by treatment with a protease, which cleaves at a site between the protease component and the translocation component. A di-chain protein is thus produced, comprising the protease component as a single polypeptide chain covalently attached (via a disulphide bridge) to another single polypeptide chain containing the translocation component plus TM. Whilst the WO 98/07864 methodology follows (in terms of structural arrangement of the fusion protein) the natural expression system of clostridial holotoxin, the present inventors have found that this system may result in the production of certain fusion proteins that have a substantially-reduced binding ability for the intended target cell.

There is therefore a need for an alternative or improved system for constructing a non-cytotoxic fusion protein.

The present invention addresses one or more of the above-mentioned problems by providing a single chain, polypeptide fusion protein, comprising:—
a. a non-cytotoxic protease, or a fragment thereof, which protease or protease fragment is capable of cleaving a protein of the exocytic fusion apparatus in a target cell;
b. a Targeting Moiety that is capable of binding to a Binding Site on the target cell, which Binding Site is capable of undergoing endocytosis to be incorporated into an endosome within the target cell;
c. a protease cleavage site at which site the fusion protein is cleavable by a protease, wherein the protease cleavage site is located between the non-cytotoxic protease or fragment thereof and the Targeting Moiety; and
a translocation domain that is capable of translocating the protease or protease fragment from within an endosome, across the endosomal membrane and into the cytosol of the target cell.

The WO98/07864 system works well for the preparation of conjugates having a TM that requires a C-terminal domain for interaction with a Binding Site on a target cell. In this regard, WO98/07864 provides fusion proteins having a C-terminal domain that is "free" to interact with a Binding Site on a target cell. The present inventors have found that this structural arrangement is not suitable for all TMs. In more detail, the present inventors have found that the WO 98/07864 fusion protein system is not optimal for TMs requiring a N-terminal domain for interaction with a binding site on a target cell. This problem is particularly acute with TMs that require a specific N-terminus amino acid residue or a specific sequence of amino acid residues including the N-terminus amino acid residue for interaction with a binding site on a target cell.

In contrast to WO98/07864, the present invention provides a system for preparing non-cytotoxic conjugates, wherein the TM component of the conjugate has an N-terminal domain (or an intra domain sequence) that is capable of binding to a Binding Site on a target cell.

The non-cytotoxic protease component of the present invention is a non-cytotoxic protease, or a fragment thereof, which protease or protease fragment is capable of cleaving different but specific peptide bonds in one of three substrate proteins, namely synaptobrevin, syntaxin or SNAP-25, of the exocytic fusion apparatus. These substrates are important components of the neurosecretory machinery. The non-cytotoxic protease component of the present invention is preferably a neisserial IgA protease or a fragment thereof or a clostridial neurotoxin L-chain or a fragment thereof. A particularly preferred non-cytotoxic protease component is a botulinum neurotoxin (BoNT) L-chain or a fragment thereof.

The translocation component of the present invention enables translocation of the non-cytotoxic protease (or fragment thereof) into the target cell such that functional expression of protease activity occurs within the cytosol of the target cell. The translocation component is preferably capable of forming ion-permeable pores in lipid membranes under conditions of low pH. Preferably it has been found to use only those portions of the protein molecule capable of pore-formation within the endosomal membrane. The translocation component may be obtained from a microbial protein source, in particular from a bacterial or viral protein source. Hence, in one embodiment, the translocation component is a translocating domain of an enzyme, such as a bacterial toxin or viral protein. The translocation component of the present invention is preferably a clostridial neurotoxin H-chain or a fragment thereof. Most preferably it is the $H_N$ domain (or a functional component thereof), wherein $H_N$ means a portion or fragment of the H-chain of a clostridial neurotoxin approximately equivalent to the amino-terminal half of the H-chain, or the domain corresponding to that fragment in the intact H-chain.

The TM component of the present invention is responsible for binding the conjugate of the present invention to a Binding Site on a target cell. Thus, the TM component is simply a ligand through which a conjugate of the present invention binds to a selected target cell.

In the context of the present invention, the target cell may be any target cell, though with the proviso that the target cell is not a nociceptive sensory afferent such as a primary sensory afferent. Thus, the TM may bind to non-neuronal cells and/or to neuronal cells.

It is routine to confirm that a TM binds to a given target cell. For example, a simple radioactive displacement experiment may be employed in which tissue or cells representative of the target cell are exposed to labelled (eg. tritiated) ligand in the presence of an excess of unlabelled ligand. In such an experiment, the relative proportions of non-specific and specific binding may be assessed, thereby allowing confirmation that the ligand binds to the target cell. Optionally, the assay may include one or more binding antagonists, and the assay may further comprise observing a loss of ligand binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

The fusion proteins of the present invention generally demonstrate a reduced binding affinity (in the region of up to 100-fold) for target cells when compared with the corresponding 'free' TM. However, despite this observation, the fusion proteins of the present invention surprisingly demonstrate good efficacy. This can be attributed to two principal features. First, the non-cytotoxic protease component is catalytic—thus, the therapeutic effect of a few such molecules is rapidly amplified.

Secondly, the receptors present on the target cells need only act as a gateway for entry of the therapeutic, and need not necessarily be stimulated to a level required in order to achieve a ligand-receptor mediated pharmacological response. Accordingly, the fusion proteins of the present invention may be administered at a dosage that is lower that would be employed for other types of therapeutic molecules, which are typically administered at high microgram to milligram (even up to hundreds of milligram) quantities. In contrast, the fusion proteins of the present invention may be administered at much lower dosages, typically at least 10-fold lower, and more typically at 100-fold lower.

The TM preferably comprises a maximum of 50 amino acid residues, more preferably a maximum of 40 amino acid residues, particularly preferably a maximum of 30 amino acid residues, and most preferably a maximum of 20 amino acid residues.

Proteinase activated receptor ligands represent a preferred group of TMs of the present invention, in particular PAR1. PARs represent a unique subtype of 7-transmembrane receptor G-protein-coupled receptors in that they are proteolytically modified to expose a new extracellular N-terminus, which acts as a tethered activating ligand. PAR1 agonists (such as TFLLR) have been identified that activate their cognate receptor.

Parathyroid hormone (PTH) also represents a preferred TM of the present invention. PTH is released by the parathyroid gland and binds to the PTH-1 receptor. This receptor has a widespread distribution but is particularly abundant in PTH target tissues, predominantly the kidney and in bone.

Thus, the most preferred TMs of the present invention are:—

| LIGAND | REFERENCE |
|---|---|
| Protease activated receptor Ligand (PAR1) | C. K. Derian, B. E. Maryanoff, P. Andrade-Gordon, and H-C Zhang DRUG DEVELOPMENT RESEARCH 59:355 (2003) |
| PTH | Shimizu M., et al 2000, J Biol Chem. Jul 21; 275(29):21836-43 |

According to one embodiment of the present invention, the TM binds to a mucus-secreting cell, or to a neuronal cell controlling or directing mucus secretion. More specifically, the TM bind to (a) cells that secrete mucins, such as epithelial goblet cells and submucosal gland mucus secreting cells, (b) cells that secrete aqueous components of mucus, such as Clara cells and serous cells, or (c) cells that control or direct mucus secretion, such as "sensory-efferent" C-fibres, or NANC neural system fibres. In this regard, particular mention is made to the TMs:—VIP; $beta_2$ adrenoreceptor agonists; gastrin-releasing peptide; and calcitonin gene related peptide. Thus, according to this embodiment, said conjugates have therapeutic application in treating mucus hypersecretion, asthma, and/or chronic obstructive pulmonary disease.

In another embodiment, the TM binds to an endocrine cell. Particular mention is made here to thyroid stimulating hormone (TSH); insulin, insulin-like growth factor; TSH releasing hormone (protirelin); FSH/LH releasing hormone (gonadorelin); corticotrophin releasing hormone (CRH); and ACTH. Thus, according to this embodiment, said conjugates have therapeutic application in treating:—endocrine neoplasia including MEN; thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome.

In another embodiment the TM binds to an inflammatory cell. Particular mention here is made to ligands (i) for mast cells, such as the C4 domain of the Fc IgE; (ii) for eosinophils, such as ligands to the C3a/C4a-R complement receptor, antigens reactive towards CR4 complement receptor; (iii) for macrophages and monocytes, such as macrophage stimulating factor, (iv) for neutrophils, such as an antigen associated with the iC3b complement receptor, or IL8. Thus, according to this embodiment, said conjugates have therapeutic application for treating allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders.

In another embodiment, the TM binds to an exocrine cell. Particular mention here is made to pituitary adenyl cyclase activating peptide (PACAP-38). Thus, according to this embodiment, said conjugates have therapeutic application for treating mucus hypersecretion from mucus-secreting cells located in the alimentary tract, in particular located in the colon.

In a further embodiment, the TM binds to an immunological cell. Mention here is made to the ligands:—Epstein Barr virus fragment/surface feature. Thus, according to this embodiment, said conjugates have therapeutic application for treating myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus.

In a further embodiment the TM binds to a cardiovascular cell. Mention here is made to thrombin and TRAP (thrombin receptor agonist peptide), and ligands that bind to cardiovascular endothelial cells such as GP1b surface antigen-recognising antibodies. Thus, according to this embodiment, said conjugates have therapeutic application for treating cardiovascular conditions and/or hypertension In a further embodiment, the TM binds to a bone cell. Mention here is made to ligands that bind to osteoblasts for the treatment of a disease selected from osteopetrosis and osteoporosis include calcitonin, and to ligands that bind to osteoclasts including osteoclast differentiation factors (eg. TRANCE, or RANKL or OPGL). Thus, according to this embodiment, said conjugates have therapeutic application for treating bone conditions.

Linear and cyclic integrin binding sequences are a preferred group of TMs of the present invention. Many integrins recognise the triple Arg-Gly-Asp (RGD) peptide sequence (Ruoslahti, 1996). The RGD motif is found in over 100 proteins including fibronectin, tenascin, fibrinogen and vitronectin. The RGD-integrin interaction is exploited as a conserved mechanism of cell entry by many pathogens including coxsackievirus (Roivaninen et al., 1991) and adenovirus (Mathias et al., 1994). The linear and cyclic peptide sequences, PLAEIDGIEL and CPLAEIDGIELC respectively, have been shown to bind and internalise DNA in cells expressing $\alpha_9\beta_1$ integrin (Schneider et al., 1999).

Other TMs of the present invention include those discovered by phage display techniques, in particular those which target and are internalised by human airway epithelial cells. These include, linear and cyclic THALWHT (Jost et al., 2001); LEBP-1 (QPFMQCLCLIYDASC), LEBP-2 (RNVPPIFNDVYWIAF) and LEBP-3 (VFRVRPWYQSTSQS) (Wu et al., 2003); CDSAFVTVDWGRSMSLC (Florea et al., 2003); SERSMNF, YGLPHKF, PSGAARA, LPHKSMP, LQHKSMP (Writer et al., 2004); FSLSKPP, HSMQLST and STQAMFQ peptides (Rahim et al., 2003).

The protease cleavage site of the present invention allows cleavage (preferably controlled cleavage) of the fusion protein at a position between the non-cytotoxic protease component and the TM component. It is this cleavage reaction that converts the fusion protein from a single chain polypeptide into a disulphide-linked, di-chain polypeptide.

According to a preferred embodiment of the present invention, the TM binds via a domain or amino acid sequence that is located away from the C-terminus of the TM. For example, the relevant binding domain may include an intra domain or an amino acid sequence located towards the middle (ie. of the linear peptide sequence) of the TM. Preferably, the relevant binding domain is located towards the N-terminus of the TM, more preferably at or near to the N-terminus.

In one embodiment, the single chain polypeptide fusion may include more than one proteolytic cleavage site. However, where two or more such sites exist, they are different, thereby substantially preventing the occurrence of multiple cleavage events in the presence of a single protease. In another embodiment, it is preferred that the single chain polypeptide fusion has a single protease cleavage site.

The protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (eg. the MapDraw program by DNAS-TAR, Inc.).

Whilst any protease cleavage site may be employed, the following are preferred:—

```
Enterokinase            (DDDDK↓)

Factor Xa               (IEGR↓/IDGR↓)

TEV(Tobacco Etch virus) (ENLYFQ↓G)

Thrombin                (LVPR↓GS)

PreScission             (LEVLFQ↓GP).
```

Also embraced by the term protease cleavage site is an intern, which is a self-cleaving sequence. The self-splicing reaction is controllable, for example by varying the concentration of reducing agent present.

In use, the protease cleavage site is cleaved and the N-terminal region (preferably the N-terminus) of the TM becomes exposed. The resulting polypeptide has a TM with an N-terminal domain or an intra domain that is substantially free from the remainder of the conjugate. This arrangement ensures that the N-terminal component (or intra domain) of the TM may interact directly with a Binding Site on a target cell.

In a preferred embodiment, the TM and the protease cleavage site are distanced apart in the fusion protein by at most 10 amino acid residues, more preferably by at most 5 amino acid residues, and most preferably by zero amino acid residues. Thus, following cleavage of the protease cleavage site, a conjugate is provided with a TM that has an N-terminal domain that is substantially free from the remainder of the conjugate. This arrangement ensures that the N-terminal component of the Targeting Moiety may interact directly with a Binding Site on a target cell.

One advantage associated with the above-mentioned activation step is that the TM only becomes susceptible to N-terminal degradation once proteolytic cleavage of the fusion protein has occurred. In addition, the selection of a specific protease cleavage site permits selective activation of the polypeptide fusion into a di-chain conformation.

Construction of the single-chain polypeptide fusion of the present invention places the protease cleavage site between the TM and the non-cytotoxic protease component.

It is preferred that, in the single-chain fusion, the TM is located between the protease cleavage site and the translocation component. This ensures that the TM is attached to the translocation domain (ie. as occurs with native clostridial holotoxin), though in the case of the present invention the order of the two components is reversed vis-à-vis native holotoxin. A further advantage with this arrangement is that the TM is located in an exposed loop region of the fusion protein, which has minimal structural effects on the conformation of the fusion protein. In this regard, said loop is variously referred to as the linker, the activation loop, the inter-domain linker, or just the surface exposed loop (Schiavo et al 2000, Phys. Rev., 80, 717-766; Turton et al., 2002, Trends Biochem. Sci., 27, 552-558).

In one embodiment, in the single chain polypeptide, the non-cytotoxic protease component and the translocation component are linked together by a disulphide bond. Thus, following cleavage of the protease cleavage site, the polypeptide assumes a di-chain conformation, wherein the protease and translocation components remain linked together by the disulphide bond. To this end, it is preferred that the protease and translocation components are distanced apart from one another in the single chain fusion protein by a maximum of 100 amino acid residues, more preferably a maximum of 80 amino acid residues, particularly preferably by a maximum of 60 amino acid residues, and most preferably by a maximum of 50 amino acid residues.

In one embodiment, the non-cytotoxic protease component forms a disulphide bond with the translocation component of the fusion protein. For example, the amino acid residue of the protease component that forms the disulphide bond is located within the last 20, preferably within the last 10 C-terminal amino acid residues of the protease component. Similarly, the amino acid residue within the translocation component that forms the second part of the disulphide bond may be located within the first 20, preferably within the first 10 N-terminal amino acid residues of the translocation component.

Alternatively, in the single chain polypeptide, the non-cytotoxic protease component and the TM may be linked together by a disulphide bond. In this regard, the amino acid residue of the TM that forms the disulphide bond is preferably located away from the N-terminus of the TM, more preferably towards to C-terminus of the TM.

In one embodiment, the non-cytotoxic protease component forms a disulphide bond with the TM component of the fusion protein. In this regard, the amino acid residue of the protease component that forms the disulphide bond is preferably located within the last 20, more preferably within the last 10 C-terminal amino acid residues of the protease component. Similarly, the amino acid residue within the TM component that forms the second part of the disulphide bond is preferably located within the last 20, more preferably within the last 10 C-terminal amino acid residues of the TM.

The above disulphide bond arrangements have the advantage that the protease and translocation components are arranged in a manner similar to that for native clostridial neurotoxin. By way of comparison, referring to the primary amino acid sequence for native clostridial neurotoxin, the respective cysteine amino acid residues are distanced apart by between 8 and 27 amino acid residues—taken from Popoff, M R & Marvaud, J-C, 1999, Structural & genomic features of clostridial neurotoxins, Chapter 9, in The Comprehensive Sourcebook of Bacterial Protein Toxins. Ed. Alouf & Freer:—

| Serotype[1] | Sequence | 'Native' length between C—C |
|---|---|---|
| BoNT/A1 | CVRGIITSKTKS----LDKGYNKALNDLC | 23 |
| BoNT/A2 | CVRGIIPFKTKS----LDEGYNKALNDLC | 23 |
| BoNT/B | CKSVKAPG------------------IC | 8 |
| BoNT/C | CHKAIDGRS----------LYNKTLDC | 15 |
| BoNT/D | CLRLTK--------------NSRDDSTC | 12 |
| BoNT/E | CKN-IVSVK----------GIRK---SIC | 13 |
| BoNT/F | CKS-VIPRK----------GTKAPP-RLC | 15 |
| BoNT/G | CKPVMYKNT----------GKSE----QC | 13 |
| TeNT | CKKIIPPTNIRENLYNRTASLTDLGGELC | 27 |

[1]Information from proteolytic strains only

The fusion protein may comprise one or more purification tags, which are located N-terminal to the protease component and/or C-terminal to the translocation component.

Whilst any purification tag may be employed, the following are preferred:—
His-tag (eg. 6× histidine), preferably as a C-terminal and/or N-terminal tag
MBP-tag (maltose binding protein), preferably as an N-terminal tag
GST-tag (glutathione-S-transferase), preferably as an N-terminal tag
His-MBP-tag, preferably as an N-terminal tag
GST-MBP-tag, preferably as an N-terminal tag
Thioredoxin-tag, preferably as an N-terminal tag
CBD-tag (Chitin Binding Domain), preferably as an N-terminal tag.

According to a further embodiment of the present invention, one or more peptide spacer molecules may be included in the fusion protein. For example, a peptide spacer may be employed between a purification tag and the rest of the fusion protein molecule (eg. between an N-terminal purification tag and a protease component of the present invention; and/or between a C-terminal purification tag and a translocation component of the present invention). A peptide spacer may be also employed between the TM and translocation components of the present invention.

In accordance with a second aspect of the present invention, there is provided a DNA sequence that encodes the above-mentioned single chain polypeptide.

In a preferred aspect of the present invention, the DNA sequence is prepared as part of a DNA vector, wherein the vector comprises a promoter and terminator.

A variety of different spacer molecules may be employed in any of the fusion proteins of the present invention. Examples of such spacer molecules include GS15, GS20, GS25, and Hx27.

The present inventors have unexpectedly found that the fusion proteins of the present invention may demonstrate an improved binding activity for target cells when the size of the spacer is selected so that (in use) the C-terminus of the TM and the N-terminus of the translocation component are separated from one another by 40-105 angstroms, preferably by 50-100 angstroms, and more preferably by 50-90 angstroms. In another embodiment, the preferred spacers have an amino acid sequence of 11-29 amino acid residues, preferably 15-27 amino acid residues, and more preferably 20-27 amino acid residues. Suitable spacers may be routinely identified and obtained according to Crasto, C. J. and Feng, J. A. (2000) May; 13(5); pp. 309-312—see also http://www.fccc./edu/research/labs/feng/limker.html.

In a preferred embodiment, the vector has a promoter selected from:

| Promoter | Induction agent | Typical induction condition |
|---|---|---|
| tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

The DNA construct of the present invention is preferably designed in silico, and then synthesised by conventional DNA synthesis techniques.

The above-mentioned DNA sequence information is optionally modified for codon-biasing according to the ultimate host cell (eg. *E. coli*) expression system that is to be employed.

The DNA backbone is preferably screened for any inherent nucleic acid sequence, which when transcribed and translated would produce an amino acid sequence corresponding to the protease cleave site encoded by the second peptide-coding sequence. This screening may be performed manually or with the assistance of computer software (eg. the MapDraw program by DNASTAR, Inc.).

According to a further embodiment of the present invention, there is provided a method of preparing a non-cytotoxic agent, comprising:—
a. contacting a single-chain polypeptide fusion protein of the invention with a protease capable of cleaving the protease cleavage site;
b. cleaving the protease cleavage site, and thereby forming a di-chain fusion protein.

This aspect provides a di-chain polypeptide, which generally mimics the structure of clostridial holotoxin. In more detail, the resulting di-chain polypeptide typically has a structure wherein:—
a. the first chain comprises the non-cytotoxic protease, or a fragment thereof, which protease or protease fragment is capable of cleaving a protein of the exocytic fusion apparatus of a target cell;
b. the second chain comprises the TM and the translocation domain that is capable of translocating the protease or protease fragment from within an endosome, across the endosomal membrane and into the cytosol of the target cell; and
the first and second chains are disulphide linked together.

According to a further aspect of the present invention, there is provided use of a single chain or di-chain polypeptide of the invention, for the manufacture of a medicament for treating, preventing or ameliorating a medical condition selected from the group consisting of mucus hypersecretion, asthma, and/or chronic obstructive pulmonary disease, endocrine neoplasia including MEN, thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome, allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders, mucus hypersecretion from mucus-secreting cells located in the alimentary tract, in particular located in the colon, myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus, cardiovascular conditions and/or hypertension, and bone conditions such as osteopetrosis and osteoporosis.

According to a related aspect, there is provided a method of treating, preventing or ameliorating a medical condition or disease in a subject, comprising administering to said patient a therapeutically effective amount of a single chain or di-chain polypeptide of the invention, wherein the medical condition or disease is selected from the group consisting of mucus hypersecretion, asthma, and/or chronic obstructive pulmonary disease, endocrine neoplasia including MEN, thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome, allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders, mucus hypersecretion from mucus-secreting cells located in the alimentary tract, in particular located in the colon, myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus, cardiovascular conditions and/or hypertension, and bone conditions such as osteopetrosis and osteoporosis.

In use, the polypeptides of the present invention are typically employed in the form of a pharmaceutical composition in association with a pharmaceutical carrier, diluent and/or excipient, although the exact form of the composition may be tailored to the mode of administration. Administration is preferably to a mammal, more preferably to a human.

The polypeptides may, for example, be employed in the form of an aerosol or nebulisable solution for inhalation or a sterile solution for parenteral administration, intra-articular administration or intra-cranial administration.

For treating endocrine targets, i.v. injection, direct injection into gland, or aerosolisation for lung delivery are preferred; for treating inflammatory cell targets, i.v. injection, sub-cutaneous injection, or surface patch administration or aerosolisation for lung delivery are preferred; for treating exocrine targets, i.v. injection, or direct injection into or direct administration to the gland or aerosolisation for lung delivery are preferred; for treating immunological targets, i.v. injection, or injection into specific tissues eg. thymus, bone marrow, or lymph tissue are preferred; for treatment of cardiovascular targets, i.v. injection is preferred; and for treatment of bone targets, i.v. injection, or direct injection is preferred. In cases of i.v. injection, this should also include the use of pump systems. In the case of compositions for treating neuronal targets, spinal injection (eg. epidural or intrathecal) or indwelling pumps may be used.

The dosage ranges for administration of the polypeptides of the present invention are those to produce the desired therapeutic effect. It will be appreciated that the dosage range required depends on the precise nature of the components, the route of administration, the nature of the formulation, the age of the patient, the nature, extent or severity of the patient's condition, contraindications, if any, and the judgement of the attending physician.

Suitable daily dosages are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly.

A particularly preferred dosing regimen is based on 2.5 ng of fusion protein as the 1× dose per kg patient. In this regard, preferred dosages are in the range 1×-100× (ie. 2.5-250 ng). This dosage range is significantly lower (ie. at least 10-fold, typically 100-fold lower) than would be employed with other types of therapeutic molecules. Moreover, the above-mentioned difference is significantly magnified when the same comparison is made on a molar basis—this is because the fusion proteins of the present invention have a considerably greater molecular weight than the conventional 'small' molecule therapeutics.

Wide variations in the required dosage, however, are to be expected depending on the precise nature of the components, and the differing efficiencies of various routes of administration. For example, oral administration would be expected to require higher dosages than administration by intravenous injection.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile vehicle. The active ingredients, depending on the vehicle and concentration used, can be either dissolved or suspended in the vehicle.

Solutions may be used for all forms of parenteral administration, and are particularly used for intravenous injection. In preparing solutions the components can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area.

Alternatively the components (ie. agent plus inhibitor) and other ingredients may be dissolved in an aqueous vehicle, the solution is sterilized by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, eg. by gamma irradiation.

Advantageously, a suspending agent for example polyvinylpyrrolidone is included in the composition/s to facilitate uniform distribution of the components.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

Definitions Section

Targeting Moiety (TM) means any chemical structure associated with an agent that functionally interacts with a Binding Site to cause a physical association between the agent and the surface of a target cell. In the context of the present invention, the target cell is any cell except a nociceptive sensory afferent. The term TM embraces any molecule (ie. a naturally occurring molecule, or a chemically/physically modified variant thereof) that is capable of binding to a Binding Site on the target cell, which Binding Site is capable of internalisation (eg. endosome formation)—also referred to as receptor-mediated endocytosis. The TM may possess an endosomal membrane translocation function, in which case separate TM and Translocation Domain components need not be present in an agent of the present invention.

The TM of the present invention binds (preferably specifically binds) to a target cell.

The term non-cytotoxic means that the protease molecule in question does not kill the target cell to which it has been re-targeted.

The protease of the present invention embraces all naturally-occurring non-cytotoxic proteases that are capable of cleaving one or more proteins of the exocytic fusion apparatus in eukaryotic cells.

The protease of the present invention is preferably a bacterial protease (or fragment thereof). More preferably the bacterial protease is selected from the genera *Clostridium* or *Neisseria* (eg. a clostridial L-chain, or a neisserial IgA protease preferably from *N. gonorrhoeae*).

The present invention also embraces modified non-cytotoxic proteases, which include amino acid sequences that do not occur in nature and/or synthetic amino acid residues, so long as the modified proteases still demonstrate the above-mentioned protease activity.

The protease of the present invention preferably demonstrates a serine or metalloprotease activity (eg. endopeptidase activity). The protease is preferably specific for a SNARE protein (eg. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

A Translocation Domain is a molecule that enables translocation of a protease (or fragment thereof) into a target cell such that a functional expression of protease activity occurs within the cytosol of the target cell. Whether any molecule (eg. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, namely the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. It is preferred that the H-chain substantially lacks the natural binding function of the $H_C$ component of the H-chain. In this regard, the $H_C$ function may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, the H-chain is preferably incapable of binding to the Binding Site on a target cell to which native clostridial neurotoxin (ie. holotoxin) binds.

In one embodiment, the translocation domain is a $H_N$ domain (or a fragment thereof) of a clostridial neurotoxin. Examples of suitable clostridial Translocation Domains include:—

| | |
|---|---|
| *Botulinum* type A neurotoxin | amino acid residues (449-871) |
| *Botulinum* type B neurotoxin | amino acid residues (441-858) |
| *Botulinum* type C neurotoxin | amino acid residues (442-866) |
| *Botulinum* type D neurotoxin | amino acid residues (446-862) |
| *Botulinum* type E neurotoxin | amino acid residues (423-845) |
| *Botulinum* type F neurotoxin | amino acid residues (440-864) |
| *Botulinum* type G neurotoxin | amino acid residues (442-863) |
| Tetanus neurotoxin | amino acid residues (458-879) |

For further details on the genetic basis of toxin production in *Clostridium botulinum* and *C. tetani*, we refer to Henderson et al (1997) in *The Clostridia: Molecular Biology and Pathogenesis, Academic press*.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin (see Table 1). Examples of non-clostridial Translocation Domain origins include, but not be restricted to, the translocation domain of diphtheria toxin [O=Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.*, 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS*, 89, pp. 7934-7938], and amphiphilic peptides [Murata et al (1992) *Biochem.*, 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral Translocation Domains suitable for use in the present invention include certain translocating domains of virally expressed membrane fusion proteins. For example, Wagner et al. (1992) and Murata et al. (1992) describe the translocation (ie. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translo-cating domain of Foamy virus envelope glycoprotein. Virally encoded Aspike proteins have particular application in the context of the present invention, for example, the E1 protein of SFV and the G protein of the G protein of VSV.

Use of the Translocation Domains listed in Table 1 includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

TABLE 1

| Translocation domain source | Amino acid Residues | References |
|---|---|---|
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGWEGMIDGWY G, and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

| SEQ ID NOs | |
|---|---|
| SEQ ID 1 | DNA sequence of the LC/A |
| SEQ ID 2 | DNA sequence of the $H_N$/A |
| SEQ ID 3 | DNA sequence of the LC/B |
| SEQ ID 4 | DNA sequence of the $H_N$/B |
| SEQ ID 5 | DNA sequence of the LC/C |
| SEQ ID 6 | DNA sequence of the $H_N$/C |
| SEQ ID 7 | DNA sequence of the CP PAR1-B linker |
| SEQ ID 8 | DNA sequence of the CP PTH-C linker |
| SEQ ID 9 | DNA sequence of the CP PAR1-B fusion |
| SEQ ID 10 | Protein sequence of the CP PAR1-B fusion |
| SEQ ID 11 | DNA sequence of the CP PTH-C fusion |
| SEQ ID 12 | Protein sequence of the CP PTH-C fusion |
| SEQ ID 13 | DNA sequence of the CP RGD-C linker |
| SEQ ID 14 | DNA sequence of the CP RGD-C fusion |
| SEQ ID 15 | Protein sequence of the CP RGD-C fusion |
| SEQ ID 16 | DNA sequence of the CP cyclicRGD-C linker |
| SEQ ID 17 | DNA sequence of the CP cyclicRGD-C fusion |
| SEQ ID 18 | Protein sequence of the CP cyclicRGD-C fusion |
| SEQ ID 19 | DNA sequence of the CP THALWHT-C linker |
| SEQ ID 20 | DNA sequence of the CP THALWHT-C fusion |
| SEQ ID 21 | Protein sequence of the CP THALWHT-C fusion |
| SEQ ID 22 | DNA sequence of the CP cyclicTHALWHT-C linker |
| SEQ ID 23 | DNA sequence of the CP cyclicTHALWHT-C fusion |
| SEQ ID 24 | Protein sequence of the CP cyclicTHALWHT-C fusion |
| SEQ ID 25 | DNA sequence of the CP ANP-C linker |
| SEQ ID 26 | DNA sequence of the CP ANP-C fusion |
| SEQ ID 27 | Protein sequence of the CP ANP-C fusion |
| SEQ ID 28 | DNA sequence of the CP VIP-C linker |
| SEQ ID 29 | DNA sequence of the CP VIP-C fusion |
| SEQ ID 30 | Protein sequence of the CP VIP-C fusion |
| SEQ ID 31 | DNA sequence of the CP Gastrin releasing peptide-C linker |
| SEQ ID 32 | DNA sequence of the CP Gastrin releasing peptide-C fusion |
| SEQ ID 33 | Protein sequence of the CP Gastrin releasing peptide-C fusion |

EXAMPLES

Example 1

Preparation of LC/B and $H_N$/B Backbone Clones

The following procedure creates the LC and $H_N$ fragments for use as the component backbone for multidomain fusion expression. This example is based on preparation of a serotype B based clone (SEQ ID3 and SEQ ID4), though the procedures and methods are equally applicable to the other serotypes (illustrated by the sequence listing for serotype A (SEQ ID1 and SEQ ID2) and serotype C (SEQ ID5 and SEQ ID6)).

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (Eg. LC/B) Insert

The LC/B (SEQ ID3) is created by one of two ways:

The DNA sequence is designed by back translation of the LC/B amino acid sequence (obtained from freely available database sources such as GenBank (accession number P10844) or Swissprot (accession locus BXB_CLOBO) using one of a variety of reverse translation software tools (for example EditSeq best *E. coli* reverse translation (DNASTAR Inc.), or Backtranslation tool v2.0 (Entelechon)). BamHI/SalI recognition sequences are incorporated at the 5' and 3' ends respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence containing the LC/B open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a Supplier (for example MWG or Sigma-Genosys) so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 µM) and a buffer appropriate for the enzyme optimised for Mg2+ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences that are not compatible with the cloning system are then removed using site directed mutagenesis (for example using Quickchange (Stratagene Inc.)).

Preparation of Translocation (Eg. $H_N$) Insert

The $H_N$/B (SEQ ID4) is created by one of two ways:

The DNA sequence is designed by back translation of the $H_N$/B amino acid sequence (obtained from freely available database sources such as GenBank (accession number P10844) or Swissprot (accession locus BXB_CLOBO)) using one of a variety of reverse translation software tools (for example EditSeq best *E. Coli* reverse translation (DNASTAR Inc.), or Backtranslation tool v2.0 (Entelechon)). A PstI restriction sequence added to the N-terminus and XbaI-stop codon-HindIII to the C-terminus ensuring the correct reading frame in maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. Coli* codon usage is maintained. *E. Coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences that are not compatible with the cloning system are then removed using site directed mutagenesis (for example using Quickchange (Stratagene Inc.)).

Example 2

Preparation of a LC/B-PAR1-$H_N$/B Fusion Protein

Preparation of Linker-PAR1-Spacer Insert

The LC-$H_N$ linker can be designed from first principle, using the existing sequence information for the linker as the template. For example, the serotype B linker defined as the inter-domain polypeptide region that exists between the cysteines of the disulphide bridge between LC and $H_N$ within which proteolytic activation occurs. This sequence information is freely available from available database sources such as GenBank (accession number P10844) or Swissprot (accession locus BXB_CLOBO). It is into this linker that an Enterokinase site, PAR1 and spacer are incorporated and using one of a variety of reverse translation software tools (for example EditSeq best *E. Coli* reverse translation (DNASTAR Inc.), or Backtranslation tool v2.0 (Entelechon)), the DNA sequence encoding the linker-ligand-spacer region is determined. Restriction site are then incorporated into the DNA sequence and can be arranged as BamHI-SalI-linker-protease site-PAR1-NheI-spacer-SpeI-PstI-XbaI-stop codon-HindIII (SEQ ID7). It is important to ensure the correct reading frame is maintained for the spacer, PAR1 and restriction sequences and that the XbaI sequence is not preceded by the bases, TC which would result on DAM methylation. The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Preparation of the LC/B-PAR1-$H_N$/B Fusion

In order to create the LC-linker-PAR1-spacer-$H_N$ construct (SEQ ID9), the pCR 4 vector encoding the linker (SEQ ID7) is cleaved with BamHI+SalI restriction enzymes. This cleaved vector then serves as the recipient vector for insertion and ligation of the LC/B DNA (SEQ ID3) cleaved with BamHI+SalI. The resulting plasmid DNA is then cleaved with PstI+XbaI restriction enzymes and serves as the recipient vector for the insertion and ligation of the $H_N$/B DNA (SEQ ID4) cleaved with PstI+XbaI. The final construct contains the LC-linker-PAR1-spacer-$H_N$ ORF (SEQ ID9) for transfer into expression vectors for expression to result in a fusion protein of the sequence illustrated in SEQ ID10.

Example 3

Preparation LC/C-PTH-$H_N$/C Fusion Protein

The LC-$H_N$ linker can be designed using the methods described in example two but using the C serotype linker arranged as BamHI-SalI-linker-protease site-PTH-NheI-spacer-SpeI-PstI-XbaI-stop codon-HindIII (SEQ ID8). The LC/C-PTH-$H_N$/C fusion is then assembled using the LC/C (SEQ ID5) and $H_N$/C (SEQ ID6) made using the methods described in example one and constructed using methods described in example two. The final construct contains the LC-linker-PTH-spacer-$H_N$ ORF (SEQ ID 11) for transfer into expression vectors for expression to result in a fusion protein of the sequence illustrated in SEQ ID 12.

Example 4

Preparation and Purification of LC/C-RGD-$H_N$/C Fusion Protein

The LC-$H_N$ linker is designed using the methods described in Example 2 but using the C serotype linker arranged as BamHI-SalI-linker-protease site-RGD-NheI-spacer-SpeI-PstI-XbaI-stop codon-HindIII (SEQ ID 13). The LC/C-RGD-$H_N$/C fusion is then assembled using the LC/C (SEQ ID 5) and $H_N$/C (SEQ ID 6) made using the methods described in Example 1 and constructed using methods described in Example 2. The final construct contains the LC-linker-RGD-spacer-$H_N$ ORF (SEQ ID 14) for transfer into expression vectors for expression to result in a fusion protein of the sequence illustrated in SEQ ID15. The resultant expression plasmid, pMAL LC/C-RGD-$H_N$/C is transformed into *E. coli* BL21 for recombinant protein expression.

Expression of LC/C-RGD-$H_N$/C Fusion Protein

Expression of the LC/C-RGD-$H_N$/C fusion protein is achieved using the following protocol. Inoculate 100 ml of modified TB containing 0.2% glucose and 100 µg/ml ampicillin in a 250 ml flask with a single colony from the LC/C-RGD-$H_N$/C expression strain. Grow the culture at 37° C., 225 rpm for 16 hours. Inoculate 1 L of modified TB containing 0.2% glucose and 100 µg/ml ampicillin in a 2 L flask with 10 ml of overnight culture. Grow cultures at 37° C. until an approximate $OD_{600nm}$ of 0.5 is reached at which point reduce the temperature to 16° C. After 1 hour induce the cultures with 1 mM IPTG and grow at 16° C. for a further 16 hours. FIG. 1 demonstrates the expressed protein in *E. coli* as analysed by SDS-PAGE.

Purification of LC/C-RGD-$H_N$/C Fusion Protein

Defrost falcon tube containing 25 ml 50 mM HEPES pH 7.2 200 mM NaCl and approximately 10 g of *E. coli* BL21 cell paste. Sonicate the cell paste on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and measure the OD of the dialysed fusion protein. Add 1 unit of factor Xa per 100 µg fusion protein and incubate at 25° C. static overnight. Load onto a 0.1 M $NiSO_4$ charged Chelating column (20-30 ml column is sufficient) equilibrated with 50 mM HEPES pH 7.2 200 mM NaCl. Wash column to baseline with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and concentrate the fusion to about 2 mg/ml, aliquot sample and freeze at −20° C. Test purified protein using OD, BCA and purity analysis. FIG. 2 demonstrates the purified protein as analysed by SDS-PAGE.

Example 5

Preparation LC/C-CyclicRGD-$H_N$/C Fusion Protein

The LC-$H_N$ linker can be designed using the methods described in Example 2 but using the C serotype linker arranged as BamHI-SalI-linker-protease site-cyclicRGD-NheI-spacer-SpeI-PstI-XbaI-stop codon-Hind III (SEQ ID16). The LC/C-cyclicRGD-$H_N$/C fusion is then assembled using the LC/C (SEQ ID5) and $H_N$/C (SEQ ID6) made using the methods described in Example 1 and constructed using methods described in Example 2. The final construct contains the LC-linker-cyclicRGD-spacer-$H_N$ ORF (SEQ ID17) for transfer into expression vectors for expression to result in a fusion protein of the sequence illustrated in SEQ ID18. The resultant expression plasmid, pMAL LC/C-cyclicRGD-$H_N$/C was transformed into *E. coli* BL21 for recombinant protein expression. Expression of the fusion protein was carried out as described in Example 4. FIG. 1 demonstrates the protein expressed in *E. coli* as analysed by SDS-PAGE.

Example 6

Preparation LC/C-THALWHT-$H_N$/C Fusion Protein

The LC-$H_N$ linker can be designed using the methods described in Example 2 but using the C serotype linker arranged as BamHI-SalI-linker-protease site-THALWHT-NheI-spacer-SpeI-PstI-XbaI-stop codon-HindIII (SEQ ID19). The LC/C-THALWHT-$H_N$/C fusion is then assembled using the LC/C (SEQ ID5) and $H_N$/C (SEQ ID6) made using the methods described in Example 1 and constructed using methods described in Example 2. The final construct contains the LC-linker-THALWHT-spacer-$H_N$ ORF (SEQ ID20) for transfer into expression vectors for expression to result in a fusion protein of the sequence illustrated in SEQ ID21. Expression of the fusion protein was carried out as described in Example 4. FIG. 1 demonstrates the protein expressed in *E. coli* as analysed by SDS-PAGE.

The THALWHT peptide sequence given in this Example (SEQ IDs 19, 20 and 21) can be exchanged with another peptide sequence found by phage display techniques. For example, LEBP-1 (QPFMQCLCLIYDASC), LEBP-2 (RNVPPIFNDVYWIAF) and LEBP-3 (VFRVRPWYQSTSQS) (Wu et al., 2003); CDSAFVTVDWGRSMSLC (Florea et al., 2003); SERSMNF, YGLPHKF, PSGAARA, LPHKSMP, LQHKSMP (Writer et al., 2004); FSLSKPP, HSMQLST and STQAMFQ peptides (Rahim et al., 2003).

Example 7

Preparation LC/C-CyclicTHALWHT-$H_N$/C Fusion Protein

The LC-$H_N$ linker can be designed using the methods described in Example 2 but using the C serotype linker arranged as BamHI-SalI-linker-protease site-cyclicTHALWHT-NheI-spacer-SpeI-PstI-XbaI-stop codon-Hind III (SEQ ID22). The LC/C-cyclicTHALWHT-$H_N$/C fusion is then assembled using the LC/C (SEQ ID5) and $H_N$/C (SEQ ID6) made using the methods described in example one and constructed using methods described in Example 2. The final construct contains the LC-linker-cyclicTHALWHT-spacer-$H_N$ ORF (SEQ ID23) for transfer into expression vectors for expression to result in a fusion protein of the sequence illustrated in SEQ ID24. Expression of the fusion protein was carried out as described in Example 4. FIG. 1 demonstrates the protein expressed in *E. coli* as analysed by SDS-PAGE.

The THALWHT peptide sequence given in this Example (SEQ IDs 19, 20 and 21) can be exchanged with another peptide sequence found by phage display techniques. For example, LEBP-1 (QPFMQCLCLIYDASC), LEBP-2 (RNVPPIFNDVYWIAF) and LEBP-3 (VFRVRPWYQSTSQS) (Wu et al., 2003); CDSAFVTVDWGRSMSLC (Florea et al., 2003); SERSMNF, YGLPHKF, PSGAARA, LPHKSMP, LQHKSMP (Writer et al., 2004); FSLSKPP, HSMQLST and STQAMFQ peptides (Rahim et al., 2003).

Example 8

Preparation LC/C-ANP-$H_N$/C Fusion Protein

The LC-$H_N$ linker can be designed using the methods described in Example 2 but using the C serotype linker arranged as BamHI-SalI-linker-protease site-ANP-NheI-spacer-SpeI-PstI-XbaI-stop codon-HindIII (SEQ ID25). The LC/C-ANP-$H_N$/C fusion is then assembled using the LC/C (SEQ ID5) and $H_N$/C (SEQ ID6) made using the methods described in Example 1 and constructed using methods described in Example 2. The final construct contains the LC-linker-ANP-spacer-$H_N$ ORF (SEQ ID26) for transfer into expression vectors for expression to result in a fusion protein of the sequence illustrated in SEQ ID27.

Example 9

Preparation LC/C-VIP-$H_N$/C Fusion Protein

The LC-$H_N$ linker can be designed using the methods described in Example 2 but using the C serotype linker arranged as BamHI-SalI-linker-protease site-VIP-NheI-spacer-SpeI-PstI-XbaI-stop codon-HindIII (SEQ ID28). The LC/C-VIP-$H_N$/C fusion is then assembled using the LC/C (SEQ ID5) and $H_N$/C (SEQ ID6) made using the methods described in Example 1 and constructed using methods described in Example 2. The final construct contains the LC-linker-VIP-spacer-$H_N$ ORF (SEQ ID29) for transfer into expression vectors for expression to result in a fusion protein of the sequence illustrated in SEQ ID30.

The VIP sequence given in SEQ ID28 could be replaced with VIP analogue or agonist sequences. For example, $[R^{15,20,21}, L^{17}]$-VIP or $[R^{15,20,21}, L^{17}]$-VIP-GRR (Kashimoto et al., 1996; Onoue et al., 2004), $[A^{2,8,9,16,19,24}]$-VIP or $[A^{2,8,9,16,19,24,25}]$-VIP (Igarashi et al., 2005).

Example 10

Preparation LC/C-Gastrin Releasing Peptide-$H_N$/C Fusion Protein

The LC-$H_N$ linker can be designed using the methods described in Example 2 but using the C serotype linker arranged as BamHI-SalI-linker-protease site-gastrin releasing peptide-NheI-spacer-SpeI-PstI-XbaI-stop codon-HindIII (SEQ ID34). The LC/C-gastrin releasing peptide-$H_N$/C fusion is then assembled using the LC/C (SEQ ID5) and H$_N$/C (SEQ ID6) made using the methods described in Example 1 and constructed using methods described in Example 2. The final construct contains the LC-linker-gastrin releasing peptide-spacer-H$_N$ORF (SEQ ID35) for transfer into expression vectors for expression to result in a fusion protein of the sequence illustrated in SEQ ID36.

Example 11

Assessment of Functionality of the LC/C-RGD-H$_N$/C Fusion Protein

The functionality of the TM component of the LC/C-RGD-H$_N$/C fusion protein (prepared according to Example 4) is assessed by a ligand binding assay. To facilitate assessment of ligand binding, an RGD binding peptide is synthesised in a biotinylated and non-biotinylated form. Binding of the fusion protein is determined by a competition assay with the biotinylated form. Briefly, NCI-H292 cells are plated into 96 well plates and viable cultures established. Cells and solutions are pre-chilled to 4° C. and solutions are prepared in cell feeding medium-plus-HEPES (50 mM). Prior to treatment, media is removed from the cells and replaced with media-plus-HEPES (500 µl per well), which is then also removed. Labelled ligand, at ×2 the required concentration, is added to all wells (50 µl per well). The fusion protein, at ×2 the required concentration, is then added to wells (50 µl per well). After 1 hour at 4° C., the media is removed and replaced with media+HEPES (100 µl per well). This media is removed and replaced with media+HEPES (100 µl per well). Cells are lysed with 100 µl per well PBS-Tween 0.1% for 5 mins at 4° C. PBS-Tween is removed and cells are washed with media+HEPES (100 µl per well). This media is removed and replaced with 100 µl PBS+100 µl streptavidin-HRP per well. Cells are incubated at RTP for 20 mins. The PBS+streptavidin is removed and the cells are washed with PBS-Tween. 100 µl per well of TMB is added and the cells are incubated at 37° C. for 10 mins. 50 µl per well 2M H$_2$SO$_4$ is added and the plate read at 450 nm. Using this methodology, the ability of the TM component of the LC/C-RGD-H$_N$/C fusion protein to bind to the cell surface is confirmed.

REFERENCES

Figure 1:
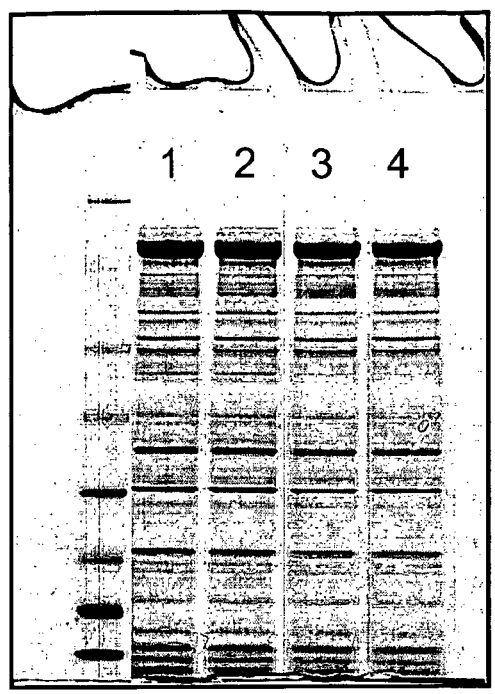
FIG. 1—Expression of LC/C-RGD-H$_N$/C, LC/C-cyclicRGD-H$_N$/C, LC/C-THALWHT-H$_N$/C and LC/C-cyclicTHALWHT-H$_N$/C fusion proteins in E. coli.
Using the methodology outlined in Example 4, LC/C-RGD-H$_N$/C, LC/C-cyclicRGD-H$_N$/C, LC/C-THALWHT-H$_N$/C and LC/C-cyclicTHALWHT-H$_N$/C fusion proteins were expressed in E. coli BL21 cells. Briefly, 1 L of TB media containing 0.2% glucose and 100 µg/ml ampicillin was inoculated with 10 ml of starter culture. Cultures were grown at 37° C. until an approximate OD$_{600nm}$ of 0.5 was reached at which point the temperature was reduced to 16° C. After 1 hour the cultures were induced with 1 mM IPTG and grown for a further 16 hours.
Lane 1, LC/C-THALWHT-H$_N$/C;
Lane 2, LC/C-RGD-H$_N$/C;
Lane 3, LC/C-cyclicTHALWHT-H$_N$/C;
Lane 4, LC/C-cyclicRGD-H$_N$/C.
Figure 2:
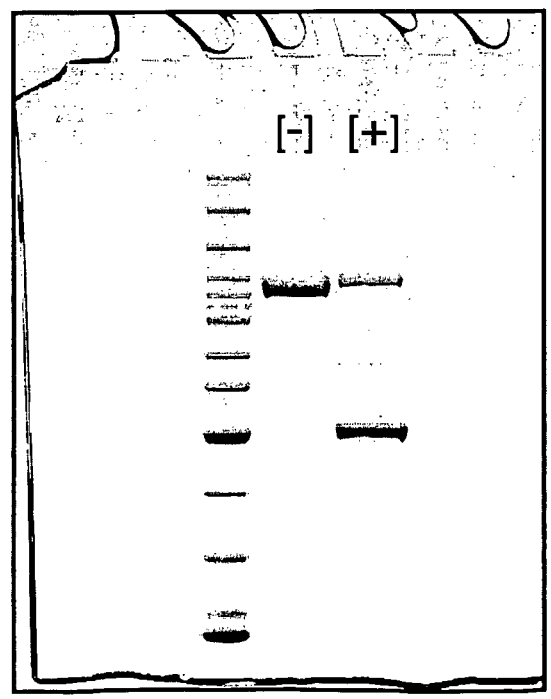
FIG. 2—Purification of a LC/C-RGD-H$_N$/C fusion protein
Using the methodology outlined in Example 5, a LC/C-RGD-H$_N$/C fusion protein was purified from E. coli BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Florea et al., (2003) J. Drug Targeting 11: 383-390
Jost et al., (2001) FEBS lett. 489: 263-269
Lee et al., (2001) Eur. J. Biochem. 268: 2004-2012
Mathias et al., (1994) J. Virol. 68: 6811-6814
Rahim et al., (2003) Biotechniques 35: 317-324
Roivaninen et al., (1991) J. Virol. 65: 4735-4740
Ruoslahti (1996) Ann. Rev. Cell Dev. Biol. 12: 697-715
Schneider et al., (1999) FEBS lett. 458: 329-332
Writer et al., (2004) J. Drug Targeting 12:185-193
Wu et al., (2003) Gene Ther. 10: 1429-1436

What is claimed is:

1. A single chain, polypeptide fusion protein having an N-terminus and a C-terminus, said fusion protein comprising:
   (a) an L-chain of a botulinum neurotoxin;
   (b) a PAR1 ligand located C-terminal of the L-chain;
   (c) a protease cleavage site at which site the fusion protein is cleavable by a protease, wherein the protease cleavage site is located between the L-chain and the PAR1 ligand; and
   (d) a translocation domain that comprises the $H_N$ domain of a botulinum neurotoxin;
   wherein the PAR1 ligand is located between the protease cleavage site and the translocation domain; and
   wherein the fusion protein lacks the natural binding function of the Hc component of a clostridial neurotoxin H-chain.

2. The fusion protein according to claim 1, wherein the fusion protein comprises a purification tag.

3. The fusion protein according to claim 2, wherein the purification tag is joined to the fusion protein by a peptide spacer molecule.

4. The fusion protein according to claim 1, wherein the translocation domain is separated from the PAR1 ligand by a peptide spacer molecule.

5. The fusion protein according to claim 1, wherein the protease cleavage site is a non-clostridial protease cleavage site selected from the group consisting of: DDDDK (SEQ ID NO: 49); IEGR (SEQ ID NO: 50); IDGR (SEQ ID NO: 51); ENLYFQG (SEQ ID NO: 52); LVPRGS (SEQ ID NO: 53); and LEVLFQGP (SEQ ID NO: 54).

6. A nucleic acid sequence encoding the polypeptide fusion protein according to claim 1.

7. A DNA vector, comprising a promoter, a nucleic acid sequence according to claim 6 located downstream of the promoter, and a terminator located downstream of said nucleic acid sequence.

* * * * *

SEQUENCE LISTING

```
<160> NUMBER OF SEQ ID NOS: 64

<210> SEQ ID NO 1
<211> LENGTH: 1302
<212> TYPE: DNA
<213> ORGANISM: Artificial Sequence
<220> FEATURE:
<223> OTHER INFORMATION: Synthetic

<400> SEQUENCE: 1
ggatccatgg agttcgttaa caaacagttc aactataaag acccagttaa cggtgttgac      60
attgcttaca tcaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
```

```
tactccaccg acctgggccg tatgctgctg actagcatcg ttcgcggtat cccgttctgg      360
ggcggttcta ccatcgatac cgaactgaaa gtaatcgaca ctaactgcat caacgttatt      420
cagccggacg gttcctatcg ttccgaagaa ctgaacctgg tgatcatcgg cccgtctgct      480
gatatcatcc agttcgagtg taagagcttt ggtcacgaag ttctgaacct cacccgtaac      540
ggctacggtt ccactcagta catccgtttc tctccggact tcaccttcgg ttttgaagaa      600
tccctggaag tagacacgaa cccactgctg gcgctggta aattcgcaac tgatcctgcg       660
gttaccctgg ctcacgaact gattcatgca ggccaccgcc tgtacggtat cgccatcaat      720
ccgaaccgtg tcttcaaagt taacaccaac gcgtattacg agatgtccgg tctggaagtt      780
agcttcgaag aactgcgtac ttttggcggt cacgacgcta aattcatcga ctctctgcaa      840
gaaaacgagt tccgtctgta ctactataac aagttcaaag atatcgcatc caccctgaac      900
aaagcgaaat ccatcgtggg taccactgct tctctccagt acatgaagaa cgttttaaa      960
gaaaaatacc tgctcagcga agacacctcc ggcaaattct ctgtagacaa gttgaaattc     1020
gataaacttt acaaaatgct gactgaaatt tacaccgaag acaacttcgt taagttcttt     1080
aaagttctga accgcaaaac ctatctgaac ttcgacaagg cagtattcaa atcaacatc      1140
gtgccgaaag ttaactacac tatctacgat ggtttcaacc tgcgtaacac caacctggct     1200
gctaatttta acggcagaa cacgaaatc aacaacatga acttcacaaa actgaaaaac       1260
ttcactggtc tgttcgagtt ttacaagctg ctgtgcgtcg ac                        1302

<210> SEQ ID NO 2
<211> LENGTH: 1257
<212> TYPE: DNA
<213> ORGANISM: Artificial Sequence
<220> FEATURE:
<223> OTHER INFORMATION: Synthetic

<400> SEQUENCE: 2
ctgcagtgta tcaaggttaa caactgggat ttattcttca gcccgagtga agacaacttc       60
accaacgacc tgaacaaagg tgaagaaatc acctcagata ctaacatcga agcagccgaa      120
gaaaacatct cgctggacct gatccagcag tactacctga cctttaattt cgacaacgag      180
ccggaaaaca tttctatcga aaacctgagc tctgatatca tcggccagct ggaactgatg      240
ccgaacatcg aacgtttccc aaacggtaaa agtacgagc tggacaaata taccatgttc       300
cactacctgc gcgcgcagga atttgaacac ggcaaatccc gtatcgcact gactaactcc      360
gttaacgaag ctctgctcaa cccgtcccgt gtatacacct tcttctctag cgactacgtg      420
aaaaaggtca caaagcgac tgaagctgca atgttcttgg gttgggttga acagcttgtt       480
tatgattta ccgacgagac gtccgaagta tctactaccg acaaaattgc ggatatcact       540
atcatcatcc cgtacatcgg tccggctctg aacattggca acatgctgta caaagacgac      600
ttcgttggcg cactgatctt ctccggtgcg gtgatcctgc tggagttcat cccggaaatc      660
gccatcccgg tactgggcac ctttgctctg gtttcttaca ttgcaaacaa ggttctgact      720
gtacaaacca tcgacaacgc gctgagcaaa cgtaacgaaa atgggatga agtttacaaa       780
tatatcgtga ccaactggct ggctaaggtt aatactcaga tcgacctcat ccgcaaaaaa      840
atgaaagaag cactggaaaa ccaggcgaa gctaccaagg caatcattaa ctaccagtac       900
aaccagtaca ccgaggaaga aaaaaacaac atcaacttca acatcgacga tctgtcctct      960
aaactgaacg aatccatcaa caaagctatg atcaacatca caagttcct gaaccagtgc      1020
tctgtaagct atctgatgaa ctccatgatc ccgtacggtg ttaaacgtct ggaggacttc     1080
```

```
gatgcgtctc tgaaagacgc cctgctgaaa tacatttacg acaaccgtgg cactctgatc    1140
ggtcaggttg atcgtctgaa ggacaaagtg aacaatacct tatcgaccga catccctttt    1200
cagctcagta aatatgtcga taaccaacgc cttttgtcca ctctagacta gaagctt       1257
```

<210> SEQ ID NO 3
<211> LENGTH: 1323
<212> TYPE: DNA
<213> ORGANISM: Artificial Sequence
<220> FEATURE:
<223> OTHER INFORMATION: Synthetic

<400> SEQUENCE: 3

```
ggatccatgc cggttaccat caacaacttc aactacaacg acccgatcga caacaacaac     60
atcattatga tggaaccgcc gttcgcacgt ggtaccggac gttactacaa ggctttaag    120 atcaccgacc gtatctggat catcccggaa cgttacacct tcggttacaa acctgaggac    180
ttcaacaaga gtagcgggat tttcaatcgt gacgtctgcg agtactatga tccagattat    240
ctgaatacca acgataagaa gaacatattc cttcagacta tgattaaact cttcaaccgt    300
atcaaaagca aaccgctcgg tgaaaaactc ctcgaaatga ttatcaacgg tatcccgtac    360
ctcggtgacc gtcgtgtccc gcttgaagag ttcaacacca acatcgcaag cgtcaccgtc    420
aacaaactca tcagcaaccc aggtgaagtc gaacgtaaaa aaggtatctt cgcaaacctc    480
atcatcttcg gtccgggtcc ggtcctcaac gaaaacgaaa ccatcgacat cggtatccag    540
aaccacttcg caagccgtga aggtttcggt ggtatcatgc agatgaaatt ctgcccggaa    600
tacgtcagtg tcttcaacaa cgtccaggaa acaaaggtg caagcatctt caaccgtcgt     660
ggttacttca gcgaccccgc actcatcctc atgcatgaac tcatccacgt cctccacggt    720
ctctacggta tcaaagttga cgacctcccg atcgtcccga acgagaagaa attcttcatg    780
cagagcaccg acgcaatcca ggctgaggaa ctctacacct tcggtggcca agacccaagt    840 atcataacccc cgtccaccga caaaagcatc tacgacaaag tcctccagaa cttcaggggt    900
atcgtggaca gactcaacaa agtcctcgtt gcatcagcg acccgaacat caatatcaac     960
atatacaaga acaagttcaa agacaagtac aaattcgtcg aggacagcga aggcaaatac    1020
agcatcgacg tagaaagttt cgacaagctc tacaaaagcc tcatgttcgg tttcaccgaa    1080
accaacatcg ccgagaacta caagatcaag acaagggcaa gttacttcag cgacagcctc    1140
ccgcctgtca aaatcaagaa cctcttagac aacgagattt acacaattga gagggcttc     1200 aacatcagtg acaaagacat ggagaaggaa tacagaggtc agaacaaggc tatcaacaaa    1260
caggcatacg aggagatcag caaagaacac ctcgcagtct acaagatcca gatgtgcgtc    1320
gac                                                                  1323
```

<210> SEQ ID NO 4
<211> LENGTH: 1260
<212> TYPE: DNA
<213> ORGANISM: Artificial Sequence
<220> FEATURE:
<223> OTHER INFORMATION: Synthetic

<400> SEQUENCE: 4

```
ctgcagtgca tcgacgttga caacgaagac ctgttcttca tcgctgacaa aaacagcttc     60
agtgacgacc tgagcaaaaa cgaacgtatc gaatacaaca cccagagcaa ctacatcgaa    120
aacgacttcc cgatcaacga actgatcctg acaccgacc tgataagtaa aatcgaactg    180
ccgagcgaaa acaccgaaag tctgaccgac ttcaacgttg acgttccggt ttacgaaaaa    240
```

| | |
|---|---|
| cagccggcta tcaagaaaat cttcaccgac gaaaacacca tcttccagta cctgtacagc | 300 |
| cagaccttcc cgctggacat ccgtgacatc agtctgacca gcagtttcga cgacgctctg | 360 |
| ctgttcagca acaaagttta cagtttcttc agcatggact acatcaaaac cgctaacaaa | 420 |
| gttgttgaag cagggctgtt cgctggttgg gttaaacaga tcgttaacga cttcgttatc | 480 |
| gaagctaaca aaagcaacac tatggacaaa atcgctgaca tcagtctgat cgttccgtac | 540 |
| atcggtctgg ctctgaacgt tggtaacgaa accgctaaag gtaactttga aaacgctttc | 600 |
| gagatcgctg gtgcaagcat cctgctggag ttcatcccgg aactgctgat cccggttgtt | 660 |
| ggtgctttcc tgctggaaag ttacatcgac aacaaaaaca gatcatcaa aaccatcgac | 720 |
| aacgctctga ccaaacgtaa cgaaaaatgg agtgatatgt acggtctgat cgttgctcag | 780 |
| tggctgagca ccgtcaacac ccagttctac accatcaaag aaggtatgta caagctctg | 840 |
| aactaccagg ctcaggctct ggaagagatc atcaaatacc gttacaacat ctacagtgag | 900 |
| aaggaaaaga gtaacatcaa catcgacttc aacgacatca cagcaaaact gaacgaaggt | 960 |
| atcaaccagg ctatcgacaa catcaacaac ttcatcaacg gttgcagtgt tagctacctg | 1020 |
| atgaagaaga tgatcccgct ggctgttgaa aaactgctgg acttcgacaa caccctgaaa | 1080 |
| aagaacctgc tgaactacat cgacgaaaac aagctgtacc tgatcggtag tgctgaatac | 1140 |
| gaaaaaagta agtgaacaa atacctgaag accatcatgc cgttcgacct gagtatctac | 1200 |
| accaacgaca ccatcctgat cgaaatgttc aacaaataca actctctaga ctagaagctt | 1260 |

<210> SEQ ID NO 5
<211> LENGTH: 1329
<212> TYPE: DNA
<213> ORGANISM: Artificial Sequence
<220> FEATURE:
<223> OTHER INFORMATION: Synthetic

<400> SEQUENCE: 5

| | |
|---|---|
| ggatccgaat tcatgccgat caccatcaac aacttcaact acagcgatcc ggtggataac | 60 |
| aaaaacatcc tgtacctgga tacccatctg aataccctgg cgaacgaacc ggaaaaagcg | 120 |
| tttcgtatca ccggcaacat ttgggttatt ccggatcgtt ttagccgtaa cagcaacccg | 180 |
| aatctgaata accgccgcg tgttaccagc ccgaaaagcg gttattacga tccgaactat | 240 |
| ctgagcaccg atagcgataa agatacctc ctgaaagaaa tcatcaaact gttcaaacgc | 300 |
| atcaacagcc gtgaaattgg cgaagaactg atctatcgcc tgagcaccga tattccgttt | 360 |
| ccgggcaaca caacaccccc gatcaacacc tttgatttcg atgtggattt caacagcgtt | 420 |
| gatgttaaaa cccgccaggg taacaattgg gtgaaaaccg gcagcattaa cccgagcgtg | 480 |
| attattaccg gtccgcgcga aaacattatt gatccggaaa ccagcacctt taaactgacc | 540 |
| aacaacacct ttgcggcgca ggaaggtttt ggcgcgctga gcattattag cattagcccg | 600 |
| cgctttatgc tgacctatag caacgcgacc aacgatgttg tgaaggccg tttcagcaaa | 660 |
| agcgaatttt gcatggaccc gatcctgatc ctgatgcatg aactgaacca tgcgatgcat | 720 |
| aacctgtatg gcatcgcgat tccgaacgat cagaccatta gcagcgtgac cagcaacatc | 780 |
| ttttacagcc agtacaacgt gaaactggaa tatgcggaaa tctatgcgtt tggcggtccg | 840 |
| accattgatc tgattccgaa aagcgcgcgc aaatacttcg aagaaaaagc gctggattac | 900 |
| tatcgcagca ttgcgaaacg tctgaacagc attaccaccg cgaatccgag cagcttcaac | 960 |
| aaatatatcg cgaatataaa acagaaactg atccgcaaat atcgctttgt ggtggaaagc | 1020 |
| agcggcgaag ttaccgttaa ccgcaataaa ttcgtggaac tgtacaacga actgaccccag | 1080 |

| | |
|---|---:|
| atcttcaccg aatttaacta tgcgaaaatc tataacgtgc agaaccgtaa aatctacctg | 1140 |
| agcaacgtgt ataccccggt gaccgcgaat attctggatg ataacgtgta cgatatccag | 1200 |
| aacggcttta acatcccgaa aagcaacctg aacgttctgt ttatgggcca gaacctgagc | 1260 |
| cgtaatccgg cgctgcgtaa agtgaacccg gaaaacatgc tgtacctgtt caccaaattt | 1320 |
| tgcgtcgac | 1329 |

<210> SEQ ID NO 6
<211> LENGTH: 1263
<212> TYPE: DNA
<213> ORGANISM: Artificial Sequence
<220> FEATURE:
<223> OTHER INFORMATION: Synthetic

<400> SEQUENCE: 6

| | |
|---|---:|
| ctgcagtgtc gtgaactgct ggtgaaaaac accgatctgc cgtttattgg cgatatcagc | 60 |
| gatgtgaaaa ccgatatctt cctgcgcaaa gatatcaacg aagaaaccga agtgatctac | 120 |
| tacccggata cgtgagcgt tgatcaggtg atcctgagca aaaacaccag cgaacatggt | 180 |
| cagctggatc tgctgtatcc gagcattgat agcgaaagcg aaattctgcc gggcgaaaac | 240 |
| caggtgtttt acgataaccg tacccagaac gtggattacc tgaacagcta ttactacctg | 300 |
| gaaagccaga aactgagcga taacgtggaa gattttacct ttacccgcag cattgaagaa | 360 |
| gcgctggata cagcgcgaa agtttacacc tattttccga ccctggcgaa caaagttaat | 420 |
| gcgggtgttc agggcggtct gtttctgatg tgggcgaacg atgtggtgga agatttcacc | 480 |
| accaacatcc tgcgtaaaga taccctggat aaaatcagcg atgttagcgc gattattccg | 540 |
| tatattggtc cggcgctgaa cattagcaat agcgtgcgtc gtggcaattt taccgaagcg | 600 |
| tttgcggtta ccggtgtgac cattctgctg gaagcgtttc cggaatttac cattccggcg | 660 |
| ctgggtgcgt ttgtgatcta tagcaaagtg caggaacgca acgaaatcat caaaaccatc | 720 |
| gataactgcc tggaacagcg tattaaacgc tggaaagata gctatgaatg gatgatgggc | 780 |
| acctggctga ccgtattat cacccagttc aacaacatca gctaccagat gtacgatagc | 840 |
| ctgaactatc aggcgggtgc gattaaagcg aaaatcgatc tggaatacaa aaaatacagc | 900 |
| ggcagcgata agaaaaacat caaaagccag gttgaaaacc tgaaaaacag cctggatgtg | 960 |
| aaaattagcg aagcgatgaa taacatcaac aaattcatcc gcaatgcag cgtgacctac | 1020 |
| ctgttcaaaa acatgctgcc gaaagtgatc gatgaactga acgaatttga tcgcaacacc | 1080 |
| aaagcgaaac tgatcaacct gatcgatagc cacaacatta ttctggtggg cgaagtggat | 1140 |
| aaactgaaag cgaaagttaa caacagcttc cagaacacca tcccgtttaa catcttcagc | 1200 |
| tataccaaca cagcctgct gaaagatatc atcaacgaat acttcaatct agactagaag | 1260 |
| ctt | 1263 |

<210> SEQ ID NO 7
<211> LENGTH: 159
<212> TYPE: DNA
<213> ORGANISM: Artificial Sequence
<220> FEATURE:
<223> OTHER INFORMATION: Synthetic

<400> SEQUENCE: 7

| | |
|---|---:|
| ggatccacgc acgtcgacga agaaaagctg tacgacgacg acgacaaaac cttttactg | 60 |
| cgtgcgctag cgggcggtgg cggtagcggc ggtggcggta gcggcggtgg cggtagcgca | 120 |
| ctagtgctgc agacgcacgg tctagaatga taaaagctt | 159 |

<210> SEQ ID NO 8
<211> LENGTH: 231
<212> TYPE: DNA
<213> ORGANISM: Artificial Sequence
<220> FEATURE:
<223> OTHER INFORMATION: Synthetic

<400> SEQUENCE: 8

```
ggatccacgc acgtcgacgc gattgatggt cgtagcgtct ctgagattca gctgatgcat      60
aatttaggca aacacttgaa tagtatggaa cgtgttgaat ggctgcgcaa aaaacttcaa     120
gatgtgcata actttgcgct agcgggcggt ggcggtagcg gcggtggcgg tagcggcggt     180
ggcggtagcg cactagtgct gcagacgcac ggtctagaat gataaaagct t              231
```

<210> SEQ ID NO 9
<211> LENGTH: 2685
<212> TYPE: DNA
<213> ORGANISM: Artificial Sequence
<220> FEATURE:
<223> OTHER INFORMATION: Synthetic

<400> SEQUENCE: 9

```
ggatccatgc cggttaccat caacaacttc aactacaacg acccgatcga caacaacaac      60
atcattatga tggaaccgcc gttcgcacgt ggtaccggac gttactacaa ggcttttaag     120
atcaccgacc gtatctggat catcccggaa cgttacacct tcggttacaa acctgaggac     180
ttcaacaaga gtagcgggat tttcaatcgt gacgtctgcg agtactatga tccagattat     240
ctgaatacca acgataagaa gaacatattc cttcagacta tgattaaaact cttcaaccgt     300 atcaaaagca aaccgctcgg tgaaaaactc ctcgaaatga ttatcaacgg tatcccgtac     360
ctcggtgacc gtcgtgtccc gcttgaagag ttcaacacca catcgcaag cgtcaccgtc     420 aacaaactca tcagcaaccc aggtgaagtc gaacgtaaaa aaggtatctt cgcaaacctc     480
atcatcttcg gtccgggtcc ggtcctcaac gaaaacgaaa ccatcgacat cggtatccag     540
aaccacttcg caagccgtga aggtttcggt ggtatcatgc agatgaaatt ctgcccggaa     600
tacgtcagtg tcttcaacaa cgtccaggaa aacaaaggtg caagcatctt caaccgtcgt     660
ggttacttca gcgacccggc actcatcctc atgcatgaac tcatccacgt cctccacggt     720
ctctacggta tcaaagttga cgacctcccg atcgtcccga acgagaagaa attcttcatg     780
cagagcaccg acgcaatcca ggctgaggaa ctctacacct tcggtggcca agacccaagt     840
atcataaccc cgtccaccga caaaagcatc tacgacaaag tcctccagaa cttcaggggt     900
atcgtggaca gactcaacaa agtcctcgtc tgcatcagcg acccgaacat caatatcaac     960
atatacaaga caagttcaa agacaagtac aaattcgtcg aggacagcga aggcaaatac    1020
agcatcgacg tagaaagttt cgacaagctc tacaaaagcc tcatgttcgg tttcaccgaa    1080
accaacatcg ccgagaacta caagatcaag acaagggcaa gttacttcag cgacagcctc    1140
ccgcctgtca aaatcaagaa cctcttagac aacgagattt acacaattga gagggcttc    1200 aacatcagtg acaaagacat ggagaaggaa tacagaggtc agaacaaggc tatcaacaaa    1260
caggcatacg aggagatcag caaagaacac ctcgcagtct acaagatcca gatgtgcgtc    1320
gacgaagaaa agctgtacga cgacgacgac aaaaaccttt tactgcgtgc gctagcgggc    1380
ggtggcggta gcggcggtgg cggtagcggc ggtggcggta gcgcactagt gctgcagtgc    1440
atcgacgttg acaacgaaga cctgttcttc atcgctgaca aaaacagctt cagtgacgac    1500
ctgagcaaaa acgaacgtat cgaatacaac acccagagca actacatcga aaacgacttc    1560
```

-continued

```
ccgatcaacg aactgatcct ggacaccgac ctgataagta aaatcgaact gccgagcgaa    1620
aacaccgaaa gtctgaccga cttcaacgtt gacgttccgg tttacgaaaa acagccggct    1680
atcaagaaaa tcttcaccga cgaaaacacc atcttccagt acctgtacag ccagaccttc    1740
ccgctggaca tccgtgacat cagtctgacc agcagtttcg acgacgctct gctgttcagc    1800
aacaaagttt acagtttctt cagcatggac tacatcaaaa ccgctaacaa agttgttgaa    1860
gcagggctgt cgctggttg ggttaaacag atcgttaacg acttcgttat cgaagctaac    1920
aaaagcaaca ctatggacaa atcgctgac atcagtctga tcgttccgta catcggtctg    1980
gctctgaacg ttggtaacga aaccgctaaa ggtaactttg aaaacgcttt cgagatcgct    2040
ggtgcaagca tcctgctgga gttcatcccg gaactgctga tcccggttgt tggtgctttc    2100
ctgctggaaa gttacatcga caacaaaaac aagatcatca aaaccatcga caacgctctg    2160
accaaacgta acgaaaaatg gagtgatatg tacggtctga tcgttgctca gtggctgagc    2220
accgtcaaca cccagttcta caccatcaaa gaaggtatgt acaaagctct gaactaccag    2280
gctcaggctc tggaagagat catcaaatac cgttacaaca tctacagtga aaggaaaaag    2340
agtaacatca acatcgactt caacgacatc aacagcaaac tgaacgaagg tatcaaccag    2400
gctatcgaca acatcaacaa cttcatcaac ggttgcagtg ttagctacct gatgaagaag    2460
atgatcccgc tggctgttga aaaactgctg gacttcgaca caccctgaa aaagaacctg    2520 ctgaactaca tcgacgaaaa caagctgtac ctgatcggta gtgctgaata cgaaaaaagt    2580
aaagtgaaca atacctgaa gaccatcatg ccgttcgacc tgagtatcta caccaacgac    2640
accatcctga tcgaaatgtt caacaaatac aactctctag actag                   2685
```

<210> SEQ ID NO 10
<211> LENGTH: 894
<212> TYPE: PRT
<213> ORGANISM: Artificial Sequence
<220> FEATURE:
<223> OTHER INFORMATION: Synthetic

<400> SEQUENCE: 10

```
Gly Ser Met Pro Val Thr Ile Asn Asn Phe Asn Tyr Asn Asp Pro Ile
1               5                   10                  15

Asp Asn Asn Asn Ile Ile Met Met Glu Pro Pro Phe Ala Arg Gly Thr
            20                  25                  30

Gly Arg Tyr Tyr Lys Ala Phe Lys Ile Thr Asp Arg Ile Trp Ile Ile
        35                  40                  45

Pro Glu Arg Tyr Thr Phe Gly Tyr Lys Pro Glu Asp Phe Asn Lys Ser
    50                  55                  60

Ser Gly Ile Phe Asn Arg Asp Val Cys Glu Tyr Tyr Asp Pro Asp Tyr
65                  70                  75                  80

Leu Asn Thr Asn Asp Lys Lys Asn Ile Phe Leu Gln Thr Met Ile Lys
                85                  90                  95

Leu Phe Asn Arg Ile Lys Ser Lys Pro Leu Gly Glu Lys Leu Leu Glu
            100                 105                 110

Met Ile Ile Asn Gly Ile Pro Tyr Leu Gly Asp Arg Arg Val Pro Leu
        115                 120                 125

Glu Glu Phe Asn Thr Asn Ile Ala Ser Val Thr Val Asn Lys Leu Ile
    130                 135                 140

Ser Asn Pro Gly Glu Val Glu Arg Lys Lys Gly Ile Phe Ala Asn Leu
145                 150                 155                 160

Ile Ile Phe Gly Pro Gly Pro Val Leu Asn Glu Asn Glu Thr Ile Asp
                165                 170                 175
```

-continued

```
Ile Gly Ile Gln Asn His Phe Ala Ser Arg Glu Gly Phe Gly Gly Ile
            180                 185                 190
Met Gln Met Lys Phe Cys Pro Glu Tyr Val Ser Val Phe Asn Asn Val
            195                 200                 205
Gln Glu Asn Lys Gly Ala Ser Ile Phe Asn Arg Arg Gly Tyr Phe Ser
210                 215                 220
Asp Pro Ala Leu Ile Leu Met His Glu Leu Ile His Val Leu His Gly
225                 230                 235                 240
Leu Tyr Gly Ile Lys Val Asp Asp Leu Pro Ile Val Pro Asn Glu Lys
                245                 250                 255
Lys Phe Phe Met Gln Ser Thr Asp Ala Ile Gln Ala Glu Glu Leu Tyr
                260                 265                 270
Thr Phe Gly Gly Gln Asp Pro Ser Ile Ile Thr Pro Ser Thr Asp Lys
                275                 280                 285
Ser Ile Tyr Asp Lys Val Leu Gln Asn Phe Arg Gly Ile Val Asp Arg
            290                 295                 300
Leu Asn Lys Val Leu Val Cys Ile Ser Asp Pro Asn Ile Asn Ile Asn
305                 310                 315                 320
Ile Tyr Lys Asn Lys Phe Lys Asp Lys Tyr Lys Phe Val Glu Asp Ser
                325                 330                 335
Glu Gly Lys Tyr Ser Ile Asp Val Glu Ser Phe Asp Lys Leu Tyr Lys
            340                 345                 350
Ser Leu Met Phe Gly Phe Thr Glu Thr Asn Ile Ala Glu Asn Tyr Lys
            355                 360                 365
Ile Lys Thr Arg Ala Ser Tyr Phe Ser Asp Ser Leu Pro Pro Val Lys
            370                 375                 380
Ile Lys Asn Leu Leu Asp Asn Glu Ile Tyr Thr Ile Glu Glu Gly Phe
385                 390                 395                 400
Asn Ile Ser Asp Lys Asp Met Glu Lys Glu Tyr Arg Gly Gln Asn Lys
                405                 410                 415
Ala Ile Asn Lys Gln Ala Tyr Glu Glu Ile Ser Lys Glu His Leu Ala
            420                 425                 430
Val Tyr Lys Ile Gln Met Cys Val Asp Glu Glu Lys Leu Tyr Asp Asp
            435                 440                 445
Asp Asp Lys Thr Phe Leu Leu Arg Ala Leu Ala Gly Gly Gly Gly Ser
450                 455                 460
Gly Gly Gly Gly Ser Gly Gly Gly Ser Ala Leu Val Leu Gln Cys
465                 470                 475                 480
Ile Asp Val Asp Asn Glu Asp Leu Phe Phe Ile Ala Asp Lys Asn Ser
                485                 490                 495
Phe Ser Asp Asp Leu Ser Lys Asn Glu Arg Ile Glu Tyr Asn Thr Gln
                500                 505                 510
Ser Asn Tyr Ile Glu Asn Asp Phe Pro Ile Asn Glu Leu Ile Leu Asp
            515                 520                 525
Thr Asp Leu Ile Ser Lys Ile Glu Leu Pro Ser Glu Asn Thr Glu Ser
            530                 535                 540
Leu Thr Asp Phe Asn Val Asp Val Pro Val Tyr Glu Lys Gln Pro Ala
545                 550                 555                 560
Ile Lys Lys Ile Phe Thr Asp Glu Asn Thr Ile Phe Gln Tyr Leu Tyr
                565                 570                 575
Ser Gln Thr Phe Pro Leu Asp Ile Arg Asp Ile Ser Leu Thr Ser Ser
            580                 585                 590
Phe Asp Asp Ala Leu Leu Phe Ser Asn Lys Val Tyr Ser Phe Phe Ser
```

|   |   |   | 595 |   |   |   | 600 |   |   |   | 605 |   |
|---|---|---|---|---|---|---|---|---|---|---|---|---|

Met Asp Tyr Ile Lys Thr Ala Asn Lys Val Val Glu Ala Gly Leu Phe
610                615                620

Ala Gly Trp Val Lys Gln Ile Val Asn Asp Phe Val Ile Glu Ala Asn
625                630                635                640

Lys Ser Asn Thr Met Asp Lys Ile Ala Asp Ile Ser Leu Ile Val Pro
        645                650                655

Tyr Ile Gly Leu Ala Leu Asn Val Gly Asn Glu Thr Ala Lys Gly Asn
        660                665                670

Phe Glu Asn Ala Phe Glu Ile Ala Gly Ala Ser Ile Leu Leu Glu Phe
        675                680                685

Ile Pro Glu Leu Leu Ile Pro Val Val Gly Ala Phe Leu Leu Glu Ser
690                695                700

Tyr Ile Asp Asn Lys Asn Lys Ile Ile Lys Thr Ile Asp Asn Ala Leu
705                710                715                720

Thr Lys Arg Asn Glu Lys Trp Ser Asp Met Tyr Gly Leu Ile Val Ala
                725                730                735

Gln Trp Leu Ser Thr Val Asn Thr Gln Phe Tyr Thr Ile Lys Glu Gly
        740                745                750

Met Tyr Lys Ala Leu Asn Tyr Gln Ala Gln Ala Leu Glu Glu Ile Ile
        755                760                765

Lys Tyr Arg Tyr Asn Ile Tyr Ser Glu Lys Glu Lys Ser Asn Ile Asn
770                775                780

Ile Asp Phe Asn Asp Ile Asn Ser Lys Leu Asn Glu Gly Ile Asn Gln
785                790                795                800

Ala Ile Asp Asn Ile Asn Asn Phe Ile Asn Gly Cys Ser Val Ser Tyr
                805                810                815

Leu Met Lys Lys Met Ile Pro Leu Ala Val Glu Lys Leu Leu Asp Phe
        820                825                830

Asp Asn Thr Leu Lys Lys Asn Leu Leu Asn Tyr Ile Asp Glu Asn Lys
        835                840                845

Leu Tyr Leu Ile Gly Ser Ala Glu Tyr Glu Lys Ser Lys Val Asn Lys
850                855                860

Tyr Leu Lys Thr Ile Met Pro Phe Asp Leu Ser Ile Tyr Thr Asn Asp
865                870                875                880

Thr Ile Leu Ile Glu Met Phe Asn Lys Tyr Asn Ser Leu Asp
                885                890

<210> SEQ ID NO 11
<211> LENGTH: 2766
<212> TYPE: DNA
<213> ORGANISM: Artificial Sequence
<220> FEATURE:
<223> OTHER INFORMATION: Synthetic

<400> SEQUENCE: 11
ggatccgaat tcatgccgat caccatcaac aacttcaact acagcgatcc ggtggataac     60
aaaaacatcc tgtacctgga tacccatctg aatccctggc gaacgaaacc ggaaaaagcg    120
tttcgtatca ccggcaacat tgggttatt ccggatcgtt ttagccgtaa cagcaacccg    180
aatctgaata aaccgccgcg tgttaccagc ccgaaaagcg gttattacga tccgaactat    240
ctgagcaccg atagcgataa agataccttc ctgaaagaaa tcatcaaact gttcaaacgc    300
atcaacagcc gtgaaattgg cgaagaactg atctatcgcc tgagcaccga tattccgttt    360
ccgggcaaca caacaccccc gatcaacacc tttgatttcg atgtggattt caacagcgtt    420

```
gatgttaaaa cccgccaggg taacaattgg gtgaaaaccg gcagcattaa cccgagcgtg    480
attattaccg gtccgcgcga aaacattatt gatccggaaa ccagcacctt taaactgacc    540
aacaacacct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt ggcggtccg     840 accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt ataccccggt gaccgcgaat attctggatg ataacgtgta cgatatccag   1200 aacggctttta acatcccgaa aagcaacctg aacgttctgt ttatgggcca gaacctgagc   1260
cgtaatccgg cgctgcgtaa agtgaacccg gaaaacatgc tgtacctgtt caccaaattt   1320
tgcgtcgacg cgattgatgg tcgtagcgtc tctgagattc agctgatgca taatttaggc   1380
aaacacttga atagtatgga acgtgttgaa tggctgcgca aaaaacttca agatgtgcat   1440
aactttgcgc tagcgggcgg tggcggtagc ggcggtggcg gtagcggcgg tggcggtagc   1500
gcactagtgc tgcagtgtcg tgaactgctg gtgaaaaaca ccgatctgcc gtttattggc   1560
gatatcagcg atgtgaaaac cgatatcttc ctgcgcaaag atatcaacga agaaaccgaa   1620
gtgatctact acccggataa cgtgagcgtt gatcaggtga tcctgagcaa aaacaccagc   1680
gaacatggtc agctggatct gctgtatccg agcattgata gcgaaagcga aattctgccg   1740
ggcgaaaacc aggtgttttta cgataaccgt acccagaacg tggattacct gaacagctat   1800
tactacctgg aaagccagaa actgagcgat aacgtggaag attttacctt tacccgcagc   1860
attgaagaag cgctggataa cagcgcgaaa gtttacacct attttccgac cctggcgaac   1920
aaagttaatg cgggtgttca gggcggtctg tttctgatgt gggcgaacga tgtggtggaa   1980
gatttcacca ccaacatcct gcgtaaagat accctggata aaatcagcga tgttagcgcg   2040
attattccgt atattggtcc ggcgctgaac attagcaata gcgtgcgtcg tggcaatttt   2100
accgaagcgt ttgcgttac cggtgtgacc attctgctgg aagcgtttcc ggaatttacc     2160
attccggcgc tgggtgcgtt tgtgatctat agcaaagtgc aggaacgcaa cgaaatcatc   2220
aaaaccatcg ataactgcct ggaacagcgt attaaacgct ggaaagatag ctatgaatgg   2280
atgatgggca cctggctgag ccgtattatc acccagttca caacatcag ctaccagatg    2340 tacgatagcc tgaactatca gcgggtgcg attaaagcga aaatcgatct ggaatacaaa    2400
aaatacagcg gcagcgataa agaaaacatc aaaagccagg ttgaaaacct gaaaaacagc   2460
ctggatgtga aaattagcga agcgatgaat aacatcaaca aattcatccg cgaatgcagc   2520
gtgacctacc tgttcaaaaa catgctgccg aaagtgatcg atgaactgaa cgaatttgat   2580
cgcaacacca aagcgaaact gatcaacctg atcgatagcc acaacattat tctggtgggc   2640
gaagtggata aactgaaagc gaaagttaac aacagcttcc agaacaccat cccgtttaac   2700
atcttcagct ataccaacaa cagcctgctg aaagatatca tcaacgaata cttcaatcta   2760
gactaa                                                              2766
```

```
<210> SEQ ID NO 12
<211> LENGTH: 921
<212> TYPE: PRT
<213> ORGANISM: Artificial Sequence
<220> FEATURE:
<223> OTHER INFORMATION: Synthetic

<400> SEQUENCE: 12
```

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr

-continued

```
                    370                 375                 380
Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                    405                 410                 415

Gln Asn Leu Ser Arg Asn Pro Ala Leu Arg Lys Val Asn Pro Glu Asn
                    420                 425                 430

Met Leu Tyr Leu Phe Thr Lys Phe Cys Val Asp Ala Ile Asp Gly Arg
                    435                 440                 445

Ser Val Ser Glu Ile Gln Leu Met His Asn Leu Gly Lys His Leu Asn
450                 455                 460

Ser Met Glu Arg Val Glu Trp Leu Arg Lys Lys Leu Gln Asp Val His
465                 470                 475                 480

Asn Phe Ala Leu Ala Gly Gly Gly Ser Gly Gly Gly Ser Gly
                    485                 490                 495

Gly Gly Gly Ser Ala Leu Val Leu Gln Cys Arg Glu Leu Leu Val Lys
                    500                 505                 510

Asn Thr Asp Leu Pro Phe Ile Gly Asp Ile Ser Asp Val Lys Thr Asp
                    515                 520                 525

Ile Phe Leu Arg Lys Asp Ile Asn Glu Glu Thr Glu Val Ile Tyr Tyr
530                 535                 540

Pro Asp Asn Val Ser Val Asp Gln Val Ile Leu Ser Lys Asn Thr Ser
545                 550                 555                 560

Glu His Gly Gln Leu Asp Leu Leu Tyr Pro Ser Ile Asp Ser Glu Ser
                    565                 570                 575

Glu Ile Leu Pro Gly Glu Asn Gln Val Phe Tyr Asp Asn Arg Thr Gln
                    580                 585                 590

Asn Val Asp Tyr Leu Asn Ser Tyr Tyr Tyr Leu Glu Ser Gln Lys Leu
                    595                 600                 605

Ser Asp Asn Val Glu Asp Phe Thr Phe Thr Arg Ser Ile Glu Glu Ala
610                 615                 620

Leu Asp Asn Ser Ala Lys Val Tyr Thr Tyr Phe Pro Thr Leu Ala Asn
625                 630                 635                 640

Lys Val Asn Ala Gly Val Gln Gly Gly Leu Phe Leu Met Trp Ala Asn
                    645                 650                 655

Asp Val Val Glu Asp Phe Thr Thr Asn Ile Leu Arg Lys Asp Thr Leu
                    660                 665                 670

Asp Lys Ile Ser Asp Val Ser Ala Ile Ile Pro Tyr Ile Gly Pro Ala
                    675                 680                 685

Leu Asn Ile Ser Asn Ser Val Arg Arg Gly Asn Phe Thr Glu Ala Phe
                    690                 695                 700

Ala Val Thr Gly Val Thr Ile Leu Leu Glu Ala Phe Pro Glu Phe Thr
705                 710                 715                 720

Ile Pro Ala Leu Gly Ala Phe Val Ile Tyr Ser Lys Val Gln Glu Arg
                    725                 730                 735

Asn Glu Ile Ile Lys Thr Ile Asp Asn Cys Leu Glu Gln Arg Ile Lys
                    740                 745                 750

Arg Trp Lys Asp Ser Tyr Glu Trp Met Met Gly Thr Trp Leu Ser Arg
                    755                 760                 765

Ile Ile Thr Gln Phe Asn Asn Ile Ser Tyr Gln Met Tyr Asp Ser Leu
                    770                 775                 780

Asn Tyr Gln Ala Gly Ala Ile Lys Ala Lys Ile Asp Leu Glu Tyr Lys
785                 790                 795                 800
```

```
Lys Tyr Ser Gly Ser Asp Lys Glu Asn Ile Lys Ser Gln Val Glu Asn
            805                 810                 815
Leu Lys Asn Ser Leu Asp Val Lys Ile Ser Glu Ala Met Asn Asn Ile
        820                 825                 830
Asn Lys Phe Ile Arg Glu Cys Ser Val Thr Tyr Leu Phe Lys Asn Met
    835                 840                 845
Leu Pro Lys Val Ile Asp Glu Leu Asn Glu Phe Asp Arg Asn Thr Lys
850                 855                 860
Ala Lys Leu Ile Asn Leu Ile Asp Ser His Asn Ile Ile Leu Val Gly
865                 870                 875                 880
Glu Val Asp Lys Leu Lys Ala Lys Val Asn Asn Ser Phe Gln Asn Thr
                885                 890                 895
Ile Pro Phe Asn Ile Phe Ser Tyr Thr Asn Asn Ser Leu Leu Lys Asp
            900                 905                 910
Ile Ile Asn Glu Tyr Phe Asn Leu Asp
        915                 920

<210> SEQ ID NO 13
<211> LENGTH: 156
<212> TYPE: DNA
<213> ORGANISM: artificial sequence
<220> FEATURE:
<223> OTHER INFORMATION: DNA sequence of the CP RGD-C linker

<400> SEQUENCE: 13
ggatccacgc acgtcgacgc gattgatggt cgtggtggtc gtggtgacat gttcggtgct      60
gcgctagcgg gcggtggcgg tagcggcggt ggcggtagcg gcggtggcgg tagcgcacta     120
gtgctgcaga cgcacggtct agaatgataa aagctt                               156

<210> SEQ ID NO 14
<211> LENGTH: 2733
<212> TYPE: DNA
<213> ORGANISM: artificial sequence
<220> FEATURE:
<223> OTHER INFORMATION: DNA sequence of the CP RGD-C fusion

<400> SEQUENCE: 14
ggatccgaat tcatgccgat caccatcaac aacttcaact acagcgatcc ggtggataac      60
aaaaacatcc tgtacctgga tacccatctg aatccctggc gaacgaaacc ggaaaaagcg     120
tttcgtatca ccggcaacat ttgggttatt ccggatcgtt ttagccgtaa cagcaacccg     180
aatctgaata accgccgcg tgttaccagc ccgaaaagcg gttattacga tccgaactat     240
ctgagcaccg atagcgataa agatacctc ctgaaagaaa tcatcaaact gttcaaacgc     300
atcaacagcc gtgaaattgg cgaagaactg atctatcgcc tgagcaccga tattccgttt     360
ccgggcaaca caacaccccc gatcaacacc tttgattcg atgtggattt caacagcgtt     420
gatgttaaaa cccgccaggg taacaattgg gtgaaaccg gcagcattaa cccgagcgtg     480
attattaccg gtccgcgcga aaacattatt gatccggaaa ccagcacctt taaactgacc     540
aacaacacct tgcggcgca ggaaggtttt ggcgcgctga gcattattag cattagcccg     600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcggaaa tctatgcgtt tggcggtccg     840
accattgatc tgattccgaa aagcgcgcgc aaatacttcg aagaaaagc gctggattac     900
```

-continued

```
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa atctacctg    1140 agcaacgtgt ataccccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccg gaaaacatgc tgtacctgtt caccaaattt   1320
tgcgtcgacg cgattgatgg tcgtggtggt cgtggtgaca tgttcggtgc tgcgctagcg   1380
ggcggtggcg gtagcggcgg tggcggtagc ggcggtggcg gtagcgcact agtgctgcag   1440
tgtcgtgaac tgctggtgaa aaacaccgat ctgccgttta ttggcgatat cagcgatgtg   1500
aaaaccgata tcttcctgcg caaagatatc aacgaagaaa ccgaagtgat ctactacccg   1560
gataacgtga gcgttgatca ggtgatcctg agcaaaaaca ccagcgaaca tggtcagctg   1620
gatctgctgt atccgagcat tgatagcgaa agcgaaattc tgccgggcga aaaccaggtg   1680
ttttacgata accgtaccca gaacgtggat tacctgaaca gctattacta cctggaaagc   1740
cagaaactga gcgataacgt ggaagatttt acctttaccc gcagcattga agaagcgctg   1800
gataacagcg cgaaagttta cacctatttt ccgaccctgg cgaacaaagt taatgcgggt   1860
gttcagggcg gtctgtttct gatgtgggcg aacgatgtgg tggaagattt caccaccaac   1920
atcctgcgta agatacccct ggataaaatc agcgatgtta gcgcgattat tccgtatatt   1980
ggtccggcgc tgaacattag caatagcgtg cgtcgtggca attttaccga agcgtttgcg   2040
gttaccggtg tgaccattct gctggaagcg tttccggaat ttaccattcc ggcgctgggt   2100
gcgtttgtga tctatagcaa agtgcaggaa cgcaacgaaa tcatcaaaac catcgataac   2160
tgcctggaac agcgtattaa acgctggaaa gatagctatg aatggatgat gggcacctgg   2220
ctgagccgta ttatcaccca gttcaacaac atcagctacc agatgtacga tagcctgaac   2280
tatcaggcgg gtgcgattaa agcgaaaatc gatctggaat acaaaaaata cagcggcagc   2340
gataaagaaa acatcaaaag ccaggttgaa aacctgaaaa acagcctgga tgtgaaaatt   2400
agcgaagcga tgaataacat caacaaattc atccgcgaat gcagcgtgac ctacctgttc   2460
aaaaacatgc tgccgaaagt gatcgatgaa ctgaacgaat tgatcgcaa caccaaagcg   2520 aaactgatca acctgatcga tagccacaac attattctgg tgggcgaagt ggataaactg   2580
aaagcgaaag ttaacaacag cttccagaac accatcccgt taacatctt cagctatacc   2640 aacaacagcc tgctgaaaga tatcatcaac gaatacttca atctagaagc actagcgagt   2700
gggcaccatc accatcacca ttaatgaaag ctt                                2733
```

<210> SEQ ID NO 15
<211> LENGTH: 909
<212> TYPE: PRT
<213> ORGANISM: artificial sequence
<220> FEATURE:
<223> OTHER INFORMATION: Protein sequence of the CP RGD-C fusion

<400> SEQUENCE: 15

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45
```

-continued

```
Val Ile Pro Asp Arg Phe Ser Arg Asn Ser Asn Pro Asn Leu Asn Lys
     50                  55                  60
Pro Pro Arg Val Thr Ser Pro Lys Ser Gly Tyr Tyr Asp Pro Asn Tyr
 65                  70                  75                  80
Leu Ser Thr Asp Ser Asp Lys Asp Thr Phe Leu Lys Glu Ile Ile Lys
                 85                  90                  95
Leu Phe Lys Arg Ile Asn Ser Arg Glu Ile Gly Glu Glu Leu Ile Tyr
                100                 105                 110
Arg Leu Ser Thr Asp Ile Pro Phe Pro Gly Asn Asn Thr Pro Ile
             115                 120                 125
Asn Thr Phe Asp Phe Asp Val Asp Phe Asn Ser Val Asp Val Lys Thr
             130                 135                 140
Arg Gln Gly Asn Asn Trp Val Lys Thr Gly Ser Ile Asn Pro Ser Val
145                 150                 155                 160
Ile Ile Thr Gly Pro Arg Glu Asn Ile Ile Asp Pro Glu Thr Ser Thr
                 165                 170                 175
Phe Lys Leu Thr Asn Asn Thr Phe Ala Ala Gln Glu Gly Phe Gly Ala
                 180                 185                 190
Leu Ser Ile Ile Ser Ile Ser Pro Arg Phe Met Leu Thr Tyr Ser Asn
             195                 200                 205
Ala Thr Asn Asp Val Gly Glu Gly Arg Phe Ser Lys Ser Glu Phe Cys
             210                 215                 220
Met Asp Pro Ile Leu Ile Leu Met His Glu Leu Asn His Ala Met His
225                 230                 235                 240
Asn Leu Tyr Gly Ile Ala Ile Pro Asn Asp Gln Thr Ile Ser Ser Val
                 245                 250                 255
Thr Ser Asn Ile Phe Tyr Ser Gln Tyr Asn Val Lys Leu Glu Tyr Ala
                 260                 265                 270
Glu Ile Tyr Ala Phe Gly Gly Pro Thr Ile Asp Leu Ile Pro Lys Ser
             275                 280                 285
Ala Arg Lys Tyr Phe Glu Glu Lys Ala Leu Asp Tyr Tyr Arg Ser Ile
             290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                 325                 330                 335
Val Val Glu Ser Ser Gly Glu Val Thr Val Asn Arg Asn Lys Phe Val
             340                 345                 350
Glu Leu Tyr Asn Glu Leu Thr Gln Ile Phe Thr Glu Phe Asn Tyr Ala
             355                 360                 365
Lys Ile Tyr Asn Val Gln Asn Arg Lys Ile Tyr Leu Ser Asn Val Tyr
             370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                 405                 410                 415
Gln Asn Leu Ser Arg Asn Pro Ala Leu Arg Lys Val Asn Pro Glu Asn
             420                 425                 430
Met Leu Tyr Leu Phe Thr Lys Phe Cys Val Asp Ala Ile Asp Gly Arg
             435                 440                 445
Gly Gly Arg Gly Asp Met Phe Gly Ala Ala Leu Ala Gly Gly Gly Gly
450                 455                 460
Ser Gly Gly Gly Gly Ser Gly Gly Gly Ser Ala Leu Val Leu Gln
```

```
            465                 470                 475                 480
Cys Arg Glu Leu Leu Val Lys Asn Thr Asp Leu Pro Phe Ile Gly Asp
                485                 490                 495

Ile Ser Asp Val Lys Thr Asp Ile Phe Leu Arg Lys Asp Ile Asn Glu
                500                 505                 510

Glu Thr Glu Val Ile Tyr Tyr Pro Asp Asn Val Ser Val Asp Gln Val
                515                 520                 525

Ile Leu Ser Lys Asn Thr Ser Glu His Gly Gln Leu Asp Leu Leu Tyr
                530                 535                 540

Pro Ser Ile Asp Ser Glu Ser Glu Ile Leu Pro Gly Glu Asn Gln Val
545                 550                 555                 560

Phe Tyr Asp Asn Arg Thr Gln Asn Val Asp Tyr Leu Asn Ser Tyr Tyr
                565                 570                 575

Tyr Leu Glu Ser Gln Lys Leu Ser Asp Asn Val Glu Asp Phe Thr Phe
                580                 585                 590

Thr Arg Ser Ile Glu Glu Ala Leu Asp Asn Ser Ala Lys Val Tyr Thr
                595                 600                 605

Tyr Phe Pro Thr Leu Ala Asn Lys Val Asn Ala Gly Val Gln Gly Gly
                610                 615                 620

Leu Phe Leu Met Trp Ala Asn Asp Val Val Glu Asp Phe Thr Thr Asn
625                 630                 635                 640

Ile Leu Arg Lys Asp Thr Leu Asp Lys Ile Ser Asp Val Ser Ala Ile
                645                 650                 655

Ile Pro Tyr Ile Gly Pro Ala Leu Asn Ile Ser Asn Ser Val Arg Arg
                660                 665                 670

Gly Asn Phe Thr Glu Ala Phe Ala Val Thr Gly Val Thr Ile Leu Leu
                675                 680                 685

Glu Ala Phe Pro Glu Phe Thr Ile Pro Ala Leu Gly Ala Phe Val Ile
                690                 695                 700

Tyr Ser Lys Val Gln Glu Arg Asn Glu Ile Ile Lys Thr Ile Asp Asn
705                 710                 715                 720

Cys Leu Glu Gln Arg Ile Lys Arg Trp Lys Asp Ser Tyr Glu Trp Met
                725                 730                 735

Met Gly Thr Trp Leu Ser Arg Ile Ile Thr Gln Phe Asn Asn Ile Ser
                740                 745                 750

Tyr Gln Met Tyr Asp Ser Leu Asn Tyr Gln Ala Gly Ala Ile Lys Ala
                755                 760                 765

Lys Ile Asp Leu Glu Tyr Lys Lys Tyr Ser Gly Ser Asp Lys Glu Asn
770                 775                 780

Ile Lys Ser Gln Val Glu Asn Leu Lys Asn Ser Leu Asp Val Lys Ile
785                 790                 795                 800

Ser Glu Ala Met Asn Asn Ile Asn Lys Phe Ile Arg Glu Cys Ser Val
                805                 810                 815

Thr Tyr Leu Phe Lys Asn Met Leu Pro Lys Val Ile Asp Glu Leu Asn
                820                 825                 830

Glu Phe Asp Arg Asn Thr Lys Ala Lys Leu Ile Asn Leu Ile Asp Ser
                835                 840                 845

His Asn Ile Ile Leu Val Gly Glu Val Asp Lys Leu Lys Ala Lys Val
                850                 855                 860

Asn Asn Ser Phe Gln Asn Thr Ile Pro Phe Asn Ile Phe Ser Tyr Thr
865                 870                 875                 880

Asn Asn Ser Leu Leu Lys Asp Ile Ile Asn Glu Tyr Phe Asn Leu Glu
                885                 890                 895
```

Ala Leu Ala Ser Gly His His His His His His Lys Leu
            900                 905

<210> SEQ ID NO 16
<211> LENGTH: 162
<212> TYPE: DNA
<213> ORGANISM: artificial sequence
<220> FEATURE:
<223> OTHER INFORMATION: DNA sequence of CP cyclicRGD-C linker

<400> SEQUENCE: 16
ggatccacgc acgtcgacgc gattgatggt cgtggtggtt gccgtggtga catgttcggt      60
tgcgctgcgc tagcgggcgg tggcggtagc ggcggtggcg tagcggcgg tggcggtagc     120 gcactagtgc tgcagacgca cggtctagaa tgataaaagc tt                       162

<210> SEQ ID NO 17
<211> LENGTH: 2739
<212> TYPE: DNA
<213> ORGANISM: artificial sequence
<220> FEATURE:
<223> OTHER INFORMATION: DNA sequence of the CP cyclicRGD-C fusion

<400> SEQUENCE: 17
ggatccgaat tcatgccgat caccatcaac aacttcaact acagcgatcc ggtggataac      60
aaaaacatcc tgtacctgga tacccatctg aatccctgg cgaacgaacc ggaaaaagcg     120
tttcgtatca ccggcaacat ttgggttatt ccggatcgtt ttagccgtaa cagcaacccg     180
aatctgaata accgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacaccccc gatcaacacc tttgatttcg atgtggattt caacagcgtt     420
gatgttaaaa cccgccaggg taacaattgg gtgaaaaccg gcagcattaa cccgagcgtg     480
attattaccg gtccgcgcga aaacattatt gatccggaaa ccagcaccct taaactgacc     540 aacaacaccct tgcggcgca ggaaggtttt ggcgcgctga gcattattag cattagcccg     600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcggaaa tctatgcgtt ggcggtccg     840 accattgatc tgattccgaa agcgcgcgc aaatacttcg aagaaaagc gctggattac     900 tatcgcagca ttgcgaaacg tctgaacagc attaccaccg cgaatccgag cagcttcaac     960
aaatatatcg gcgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa atctacctg    1140 agcaacgtgt ataccccggt gaccgcgaat attctggatg ataacgtgta cgatatccag    1200 aacggctta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg cgattgatgg tcgtggtggt tgccgtggtg acatgttcgg ttgcgctgcg    1380
ctagcgggcg gtggcggtag cggcggtggc gtagcggcg gtggcggtag cgcactagtg    1440
ctgcagtgtc gtgaactgct ggtgaaaaac accgatctgc gtttattgg cgatatcagc    1500 gatgtgaaaa ccgatatctt cctgcgcaaa gatatcaacg aagaaaccga agtgatctac    1560

```
tacccggata acgtgagcgt tgatcaggtg atcctgagca aaaacaccag cgaacatggt    1620
cagctggatc tgctgtatcc gagcattgat agcgaaagcg aaattctgcc gggcgaaaac    1680
caggtgtttt acgataaccg tacccagaac gtggattacc tgaacagcta ttactacctg    1740
gaaagccaga aactgagcga taacgtggaa gattttacct ttacccgcag cattgaagaa    1800 cgctggata cagcgcgaa agtttacacc tattttccga ccctggcgaa caaagttaat    1860
gcgggtgttc agggcggtct gtttctgatg tgggcgaacg atgtggtgga agatttcacc    1920
accaacatcc tgcgtaaaga taccctggat aaaatcagcg atgttagcgc gattattccg    1980
tatattggtc cggcgctgaa cattagcaat agcgtgcgtc gtggcaattt taccgaagcg    2040
tttgcggtta ccggtgtgac cattctgctg aagcgtttc cggaatttac cattccggcg    2100
ctgggtgcgt ttgtgatcta tagcaaagtg caggaacgca cgaaatcat caaaaccatc    2160 gataactgcc tggaacagcg tattaaacgc tggaaagata gctatgaatg gatgatgggc    2220
acctggctga gccgtattat cacccagttc aacaacatca gctaccagat gtacgatagc    2280
ctgaactatc aggcgggtgc gattaaagcg aaaatcgatc tggaatacaa aaaatacagc    2340
ggcagcgata agaaaaacat caaaagccag gttgaaaacc tgaaaaacag cctggatgtg    2400
aaaattagcg aagcgatgaa taacatcaac aaattcatcc gcgaatgcag cgtgacctac    2460
ctgttcaaaa acatgctgcc gaaagtgatc gatgaactga cgaatttga tcgcaacacc    2520 aaagcgaaac tgatcaacct gatcgatagc cacaacatta ttctggtggg cgaagtggat    2580
aaactgaaag cgaaagttaa caacagcttc agaacacca tcccgtttaa catcttcagc    2640
tataccaaca acagcctgct gaaagatatc atcaacgaat acttcaatct agaagcacta    2700
gcgagtgggc accatcacca tcaccattaa tgaaagctt                          2739
```

<210> SEQ ID NO 18
<211> LENGTH: 911
<212> TYPE: PRT
<213> ORGANISM: artificial sequence
<220> FEATURE:
<223> OTHER INFORMATION: Protein sequence of the CP cyclicRGD-C fusion

<400> SEQUENCE: 18

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160
```

```
Ile Ile Thr Gly Pro Arg Glu Asn Ile Ile Asp Pro Glu Thr Ser Thr
            165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
            195                 200                 205

Ala Thr Asn Asp Val Gly Glu Gly Arg Phe Ser Lys Ser Glu Phe Cys
            210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
            245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
            275                 280                 285

Ala Arg Lys Tyr Phe Glu Glu Lys Ala Leu Asp Tyr Tyr Arg Ser Ile
            290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
            325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
            355                 360                 365

Lys Ile Tyr Asn Val Gln Asn Arg Lys Ile Tyr Leu Ser Asn Val Tyr
            370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
            405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
            435                 440                 445

Gly Gly Cys Arg Gly Asp Met Phe Gly Cys Ala Ala Leu Ala Gly Gly
            450                 455                 460

Gly Gly Ser Gly Gly Gly Ser Gly Gly Gly Ser Ala Leu Val
465                 470                 475                 480

Leu Gln Cys Arg Glu Leu Leu Val Lys Asn Thr Asp Leu Pro Phe Ile
            485                 490                 495

Gly Asp Ile Ser Asp Val Lys Thr Asp Ile Phe Leu Arg Lys Asp Ile
            500                 505                 510

Asn Glu Glu Thr Glu Val Ile Tyr Tyr Pro Asp Asn Val Ser Val Asp
            515                 520                 525

Gln Val Ile Leu Ser Lys Asn Thr Ser Glu His Gly Gln Leu Asp Leu
            530                 535                 540

Leu Tyr Pro Ser Ile Asp Ser Glu Ser Glu Ile Leu Pro Gly Glu Asn
545                 550                 555                 560

Gln Val Phe Tyr Asp Asn Arg Thr Gln Asn Val Asp Tyr Leu Asn Ser
            565                 570                 575

Tyr Tyr Tyr Leu Glu Ser Gln Lys Leu Ser Asp Asn Val Glu Asp Phe
```

```
                        580                 585                 590
Thr Phe Thr Arg Ser Ile Glu Glu Ala Leu Asp Asn Ser Ala Lys Val
                595                 600                 605

Tyr Thr Tyr Phe Pro Thr Leu Ala Asn Lys Val Asn Ala Gly Val Gln
            610                 615                 620

Gly Gly Leu Phe Leu Met Trp Ala Asn Asp Val Val Glu Asp Phe Thr
625                 630                 635                 640

Thr Asn Ile Leu Arg Lys Asp Thr Leu Ser Lys Ile Ser Asp Val Ser
                645                 650                 655

Ala Ile Ile Pro Tyr Ile Gly Pro Ala Leu Asn Ile Ser Asn Ser Val
            660                 665                 670

Arg Arg Gly Asn Phe Thr Glu Ala Phe Ala Val Thr Gly Val Thr Ile
            675                 680                 685

Leu Leu Glu Ala Phe Pro Glu Phe Thr Ile Pro Ala Leu Gly Ala Phe
            690                 695                 700

Val Ile Tyr Ser Lys Val Gln Glu Arg Asn Glu Ile Ile Lys Thr Ile
705                 710                 715                 720

Asp Asn Cys Leu Glu Gln Arg Ile Lys Arg Trp Lys Asp Ser Tyr Glu
                725                 730                 735

Trp Met Met Gly Thr Trp Leu Ser Arg Ile Ile Thr Gln Phe Asn Asn
                740                 745                 750

Ile Ser Tyr Gln Met Tyr Asp Ser Leu Asn Tyr Gln Ala Gly Ala Ile
            755                 760                 765

Lys Ala Lys Ile Asp Leu Glu Tyr Lys Tyr Ser Gly Ser Asp Lys
            770                 775                 780

Glu Asn Ile Lys Ser Gln Val Glu Asn Leu Lys Asn Ser Leu Asp Val
785                 790                 795                 800

Lys Ile Ser Glu Ala Met Asn Asn Ile Asn Lys Phe Ile Arg Glu Cys
                805                 810                 815

Ser Val Thr Tyr Leu Phe Lys Asn Met Leu Pro Lys Val Ile Asp Glu
                820                 825                 830

Leu Asn Glu Phe Asp Arg Asn Thr Lys Ala Lys Leu Ile Asn Leu Ile
            835                 840                 845

Asp Ser His Asn Ile Ile Leu Val Gly Glu Val Asp Lys Leu Lys Ala
850                 855                 860

Lys Val Asn Asn Ser Phe Gln Asn Thr Ile Pro Phe Asn Ile Phe Ser
865                 870                 875                 880

Tyr Thr Asn Asn Ser Leu Leu Lys Asp Ile Ile Asn Glu Tyr Phe Asn
                885                 890                 895

Leu Glu Ala Leu Ala Ser Gly His His His His His His Lys Leu
            900                 905                 910

<210> SEQ ID NO 19
<211> LENGTH: 150
<212> TYPE: DNA
<213> ORGANISM: artificial sequence
<220> FEATURE:
<223> OTHER INFORMATION: DNA sequence of the CP THALWHT-C linker

<400> SEQUENCE: 19
ggatccacgc acgtcgacgc gattgatggt cgtactcacg ctctgtggca caccgcgcta      60
gcgggcggtg gcggtagcgg cggtggcggt agcggcggtg gcggtagcgc actagtgctg     120
cagacgcacg gtctagaatg ataaaagctt                                     150

<210> SEQ ID NO 20
```

<211> LENGTH: 2727
<212> TYPE: DNA
<213> ORGANISM: artificial sequence
<220> FEATURE:
<223> OTHER INFORMATION: DNA sequence of the CP THALWHT-C fusion

<400> SEQUENCE: 20
ggatccgaat tcatgccgat caccatcaac aacttcaact acagcgatcc ggtggataac 60
aaaaacatcc tgtacctgga tacccatctg aataccctgg cgaacgaacc ggaaaaagcg 120
tttcgtatca ccggcaacat ttgggttatt ccggatcgtt ttagccgtaa cagcaacccg 180
aatctgaata aaccgccgcg tgttaccagc ccgaaaagcg gttattacga tccgaactat 240
ctgagcaccg atagcgataa agataccttc ctgaaagaaa tcatcaaact gttcaaacgc 300
atcaacagcc gtgaaattgg cgaagaactg atctatcgcc tgagcaccga tattccgttt 360
ccgggcaaca acaacacccc gatcaacacc tttgatttcg atgtggattt caacagcgtt 420
gatgttaaaa cccgccaggg taacaattgg gtgaaaaccg gcagcattaa cccgagcgtg 480
attattaccg gtccgcgcga aaacattatt gatccggaaa ccagcacctt taaactgacc 540
aacaacacct ttgcggcgca ggaaggtttt ggcgcgctga gcattattag cattagcccg 600
cgctttatgc tgacctatag caacgcgacc aacgatgttg gtgaaggccg tttcagcaaa 660
agcgaatttt gcatggaccc gatcctgatc ctgatgcatg aactgaacca tgcgatgcat 720
aacctgtatg gcatcgcgat tccgaacgat cagaccatta gcagcgtgac cagcaacatc 780
ttttacagcc agtacaacgt gaaactggaa tatgcggaaa tctatgcgtt tggcggtccg 840
accattgatc tgattccgaa aagcgcgcgc aaatacttcg aagaaaaagc gctggattac 900
tatcgcagca ttgcgaaacg tctgaacagc attaccaccg cgaatccgag cagcttcaac 960
aaatatatcg gcgaatataa acagaaactg atccgcaaat atcgctttgt ggtggaaagc 1020
agcggcgaag ttaccgttaa ccgcaataaa ttcgtggaac tgtacaacga actgacccag 1080
atcttcaccg aatttaacta tgcgaaaatc tataacgtgc agaaccgtaa aatctacctg 1140
agcaacgtgt ataccccggt gaccgcgaat attctggatg ataacgtgta cgatatccag 1200
aacggcttta acatcccgaa aagcaacctg aacgttctgt ttatgggcca gaacctgagc 1260
cgtaatccgg cgctgcgtaa agtgaacccg gaaaacatgc tgtacctgtt caccaaattt 1320
tgcgtcgacg cgattgatgg tcgtactcac gctctgtggc acaccgcgct agcgggcggt 1380
ggcggtagcg gcggtggcgg tagcggcggt ggcggtagcg cactagtgct gcagtgtcgt 1440
gaactgctgg tgaaaaacac cgatctgccg tttattggcg atatcagcga tgtgaaaacc 1500
gatatcttcc tgcgcaaaga tatcaacgaa gaaaccgaag tgatctacta cccggataac 1560
gtgagcgttg atcaggtgat cctgagcaaa aacaccagcg aacatggtca gctggatctg 1620
ctgtatccga gcattgatag cgaaagcgaa attctgccgg gcgaaaacca ggtgttttac 1680
gataaccgta cccagaacgt ggattacctg aacagctatt actacctgga aagccagaaa 1740
ctgagcgata acgtggaaga ttttaccttt acccgcagca ttgaagaagc gctggataac 1800
agcgcgaaag tttacaccta ttttccgacc ctggcgaaca aagttaatgc gggtgttcag 1860
ggcggtctgt ttctgatgtg ggcgaacgat gtggtggaag atttcaccac caacatcctg 1920
cgtaaagata ccctggataa aatcagcgat gttagcgcga ttattccgta tattggtccg 1980
gcgctgaaca ttagcaatag cgtgcgtcgt ggcaatttta ccgaagcgtt tgcggttacc 2040
ggtgtgacca ttctgctgga agcgtttccg gaatttacca ttccggcgct gggtgcgttt 2100
gtgatctata gcaaagtgca ggaacgcaac gaaatcatca aaaccatcga taactgcctg 2160

```
gaacagcgta ttaaacgctg gaaagatagc tatgaatgga tgatgggcac ctggctgagc    2220
cgtattatca cccagttcaa caacatcagc taccagatgt acgatagcct gaactatcag    2280
gcgggtgcga ttaaagcgaa atcgatctg gaatacaaaa atacagcgg cagcgataaa    2340 gaaaacatca aaagccaggt tgaaaacctg aaaaacagcc tggatgtgaa aattagcgaa    2400
gcgatgaata acatcaacaa attcatccgc gaatgcagcg tgacctacct gttcaaaaac    2460
atgctgccga agtgatcga tgaactgaac gaatttgatc gcaacaccaa agcgaaactg    2520
atcaacctga tcgatagcca acacattatt ctggtgggcg aagtggataa actgaaagcg    2580
aaagttaaca acagcttcca gaacaccatc ccgtttaaca tcttcagcta taccaacaac    2640
agcctgctga agatatcat caacgaatac ttcaatctag aagcactagc gagtgggcac    2700
catcaccatc accattaatg aaagctt                                        2727

<210> SEQ ID NO 21
<211> LENGTH: 907
<212> TYPE: PRT
<213> ORGANISM: artificial sequence
<220> FEATURE:
<223> OTHER INFORMATION: Protein sequence of the CP THALWHT-C fusion

<400> SEQUENCE: 21

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
                20                  25                  30

Leu Ala Asn Glu Pro Glu Lys Ala Phe Arg Ile Thr Gly Asn Ile Trp
            35                  40                  45

Val Ile Pro Asp Arg Phe Ser Arg Asn Ser Asn Pro Asn Leu Asn Lys
        50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
                100                 105                 110

Arg Leu Ser Thr Asp Ile Pro Phe Pro Gly Asn Asn Asn Thr Pro Ile
            115                 120                 125

Asn Thr Phe Asp Phe Asp Val Asp Phe Asn Ser Val Asp Val Lys Thr
130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
                180                 185                 190

Leu Ser Ile Ile Ser Ile Ser Pro Arg Phe Met Leu Thr Tyr Ser Asn
            195                 200                 205

Ala Thr Asn Asp Val Gly Glu Gly Arg Phe Ser Lys Ser Glu Phe Cys
        210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
                260                 265                 270
```

```
Glu Ile Tyr Ala Phe Gly Gly Pro Thr Ile Asp Leu Ile Pro Lys Ser
            275                 280                 285

Ala Arg Lys Tyr Phe Glu Glu Lys Ala Leu Asp Tyr Tyr Arg Ser Ile
290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
            325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
            355                 360                 365

Lys Ile Tyr Asn Val Gln Asn Arg Lys Ile Tyr Leu Ser Asn Val Tyr
            370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
            405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
            435                 440                 445

Thr His Ala Leu Trp His Thr Ala Leu Ala Gly Gly Gly Ser Gly
            450                 455                 460

Gly Gly Gly Ser Gly Gly Gly Gly Ser Ala Leu Val Leu Gln Cys Arg
465                 470                 475                 480

Glu Leu Leu Val Lys Asn Thr Asp Leu Pro Phe Ile Gly Asp Ile Ser
            485                 490                 495

Asp Val Lys Thr Asp Ile Phe Leu Arg Lys Asp Ile Asn Glu Glu Thr
            500                 505                 510

Glu Val Ile Tyr Tyr Pro Asp Asn Val Ser Val Asp Gln Val Ile Leu
            515                 520                 525

Ser Lys Asn Thr Ser Glu His Gly Gln Leu Asp Leu Leu Tyr Pro Ser
530                 535                 540

Ile Asp Ser Glu Ser Glu Ile Leu Pro Gly Glu Asn Gln Val Phe Tyr
545                 550                 555                 560

Asp Asn Arg Thr Gln Asn Val Asp Tyr Leu Asn Ser Tyr Tyr Tyr Leu
            565                 570                 575

Glu Ser Gln Lys Leu Ser Asp Asn Val Glu Asp Phe Thr Phe Thr Arg
            580                 585                 590

Ser Ile Glu Glu Ala Leu Asp Asn Ser Ala Lys Val Tyr Thr Tyr Phe
            595                 600                 605

Pro Thr Leu Ala Asn Lys Val Asn Ala Gly Val Gln Gly Gly Leu Phe
610                 615                 620

Leu Met Trp Ala Asn Asp Val Val Glu Asp Phe Thr Thr Asn Ile Leu
625                 630                 635                 640

Arg Lys Asp Thr Leu Asp Lys Ile Ser Asp Val Ser Ala Ile Ile Pro
            645                 650                 655

Tyr Ile Gly Pro Ala Leu Asn Ile Ser Asn Ser Val Arg Arg Gly Asn
            660                 665                 670

Phe Thr Glu Ala Phe Ala Val Thr Gly Val Thr Ile Leu Leu Glu Ala
            675                 680                 685

Phe Pro Glu Phe Thr Ile Pro Ala Leu Gly Ala Phe Val Ile Tyr Ser
```

```
                690              695              700
Lys Val Gln Glu Arg Asn Glu Ile Ile Lys Thr Ile Asp Asn Cys Leu
705              710              715              720

Glu Gln Arg Ile Lys Arg Trp Lys Asp Ser Tyr Glu Trp Met Met Gly
                725              730              735

Thr Trp Leu Ser Arg Ile Ile Thr Gln Phe Asn Asn Ile Ser Tyr Gln
                740              745              750

Met Tyr Asp Ser Leu Asn Tyr Gln Ala Gly Ala Ile Lys Ala Lys Ile
                755              760              765

Asp Leu Glu Tyr Lys Lys Tyr Ser Gly Ser Asp Lys Glu Asn Ile Lys
        770              775              780

Ser Gln Val Glu Asn Leu Lys Asn Ser Leu Asp Val Lys Ile Ser Glu
785              790              795              800

Ala Met Asn Asn Ile Asn Lys Phe Ile Arg Glu Cys Ser Val Thr Tyr
                805              810              815

Leu Phe Lys Asn Met Leu Pro Lys Val Ile Asp Glu Leu Asn Glu Phe
        820              825              830

Asp Arg Asn Thr Lys Ala Lys Leu Ile Asn Leu Ile Asp Ser His Asn
        835              840              845

Ile Ile Leu Val Gly Glu Val Asp Lys Leu Lys Ala Lys Val Asn Asn
850              855              860

Ser Phe Gln Asn Thr Ile Pro Phe Asn Ile Phe Ser Tyr Thr Asn Asn
865              870              875              880

Ser Leu Leu Lys Asp Ile Ile Asn Glu Tyr Phe Asn Leu Glu Ala Leu
                885              890              895

Ala Ser Gly His His His His His His Lys Leu
                900              905

<210> SEQ ID NO 22
<211> LENGTH: 156
<212> TYPE: DNA
<213> ORGANISM: artificial sequence
<220> FEATURE:
<223> OTHER INFORMATION: DNA sequence of the CP cyclicTHALWHT-C linker

<400> SEQUENCE: 22
ggatccacgc acgtcgacgc gattgatggt cgttgtactc acgctctgtg gcacacctgc      60
gcgctagcgg gcggtggcgg tagcggcggt ggcggtagcg gcggtggcgg tagcgcacta     120
gtgctgcaga cgcacggtct agaatgataa aagctt                               156

<210> SEQ ID NO 23
<211> LENGTH: 2733
<212> TYPE: DNA
<213> ORGANISM: artificial sequence
<220> FEATURE:
<223> OTHER INFORMATION: DNA sequence of the CP cyclicTHALWHT-C fusion

<400> SEQUENCE: 23
ggatccgaat tcatgccgat caccatcaac aacttcaact acagcgatcc ggtggataac      60
aaaaacatcc tgtacctgga tacccatctg aataccctgg cgaacgaacc ggaaaaagcg     120
tttcgtatca ccggcaacat tgggttatt ccggatcgtt ttagccgtaa cagcaacccg      180
aatctgaata aaccgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacacccc gatcaacacc tttgatttcg atgtggattt caacagcgtt     420
```

```
gatgttaaaa cccgccaggg taacaattgg gtgaaaaccg gcagcattaa cccgagcgtg      480
attattaccg gtccgcgcga aacattatt gatccggaaa ccagcaccta taaactgacc       540
aacaacacct ttgcggcgca ggaaggtttt ggcgcgctga gcattattag cattagcccg      600
cgctttatgc tgacctatag caacgcgacc aacgatgttg gtgaaggccg tttcagcaaa      660
agcgaatttt gcatggaccc gatcctgatc ctgatgcatg aactgaacca tgcgatgcat      720
aacctgtatg gcatcgcgat tccgaacgat cagaccatta gcagcgtgac cagcaacatc      780
ttttacagcc agtacaacgt gaaactggaa tatgcgaaaa tctatgcgtt tggcggtccg      840
accattgatc tgattccgaa aagcgcgcgc aaatacttcg aagaaaaagc gctggattac      900
tatcgcagca ttgcgaaacg tctgaacagc attaccaccg cgaatccgag cagcttcaac      960
aaatatatcg gcgaatataa acagaaactg atccgcaaat atcgctttgt ggtggaaagc     1020
agcggcgaag ttaccgttaa ccgcaataaa ttcgtggaac tgtacaacga actgacccag     1080
atcttcaccg aatttaacta tgcgaaaatc tataacgtgc agaaccgtaa aatctacctg     1140
agcaacgtgt ataccccggt gaccgcgaat attctggatg ataacgtgta cgatatccag     1200
aacggcttta acatcccgaa aagcaacctg aacgttctgt ttatgggcca gaacctgagc     1260
cgtaatccgg cgctgcgtaa agtgaacccg gaaaacatgc tgtacctgtt caccaaattt     1320
tgcgtcgacg cgattgatgg tcgttgtact cacgctctgt ggcacacctg cgcgctagcg     1380
ggcggtggcg gtagcggcgg tggcggtagc ggcggtggcg gtagcgcact agtgctgcag     1440
tgtcgtgaac tgctggtgaa aaacaccgat ctgccgttta ttggcgatat cagcgatgtg     1500
aaaaccgata tcttcctgcg caaagatatc aacgaagaaa ccgaagtgat ctactacccg     1560
gataacgtga gcgttgatca ggtgatcctg agcaaaaaca ccagcgaaca tggtcagctg     1620
gatctgctgt atccgagcat tgatagcgaa agcgaaattc tgccgggcga aaaccaggtg     1680
ttttacgata accgtaccca gaacgtggat tacctgaaca gctattacta cctggaaagc     1740
cagaaactga gcgataacgt ggaagatttt acctttaccc gcagcattga agaagcgctg     1800
gataacagcg cgaaagttta cacctatttt ccgacccctgg cgaacaaagt taatgcgggt     1860
gttcagggcg gtctgtttct gatgtgggcg aacgatgtgg tggaagattt caccaccaac     1920
atcctgcgta aagatacct ggataaaatc agcgatgtta gcgcgattat tccgtatatt     1980
ggtccggcgc tgaacattag caatagcgtg cgtcgtggca ttttaccga agcgtttgcg      2040 gttaccggtg tgaccattct gctggaagcg tttccggaat ttaccattcc ggcgctgggt     2100
gcgtttgtga tctatagcaa agtgcaggaa cgcaacgaaa tcatcaaaac catcgataac     2160
tgcctggaac agcgtattaa acgctggaaa gatagctatg aatggatgat gggcaccctgg    2220 ctgagccgta ttatcaccca gttcaacaac atcagctacc agatgtacga tagcctgaac     2280
tatcaggcgg gtgcgattaa agcgaaaatc gatctggaat acaaaaaata cagcggcagc     2340
gataaagaaa acatcaaaag ccaggttgaa aacctgaaaa acagcctgga tgtgaaaatt     2400
agcgaagcga tgaataacat caacaaattc atccgcgaat gcagcgtgac ctacctgttc     2460
aaaaacatgc tgccgaaagt gatcgatgaa ctgaacgaat tgatcgcaa caccaaagcg     2520 aaactgatca acctgatcga tagccacaac attattctgg tgggcgaagt ggataaactg     2580
aaagcgaaag ttaacaacag cttccagaac accatcccgt taacatctt cagctatacc     2640 aacaacagcc tgctgaaaga tatcatcaac gaatacttca atctagaagc actagcgagt     2700
gggcaccatc accatcacca ttaatgaaag ctt                                  2733
```

-continued

<210> SEQ ID NO 24
<211> LENGTH: 909
<212> TYPE: PRT
<213> ORGANISM: artificial sequence
<220> FEATURE:
<223> OTHER INFORMATION: Protein sequence of the CP cyclicTHALWHT-C
      fusion

<400> SEQUENCE: 24

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Ar

-continued

```
                370                 375                 380
Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
                420                 425                 430

Met Leu Tyr Leu Phe Thr Lys Phe Cys Val Asp Ala Ile Asp Gly Arg
                435                 440                 445

Cys Thr His Ala Leu Trp His Thr Cys Ala Leu Ala Gly Gly Gly Gly
                450                 455                 460

Ser Gly Gly Gly Gly Ser Gly Gly Gly Gly Ser Ala Leu Val Leu Gln
465                 470                 475                 480

Cys Arg Glu Leu Leu Val Lys Asn Thr Asp Leu Pro Phe Ile Gly Asp
                485                 490                 495

Ile Ser Asp Val Lys Thr Asp Ile Phe Leu Arg Lys Asp Ile Asn Glu
                500                 505                 510

Glu Thr Glu Val Ile Tyr Tyr Pro Asp Asn Val Ser Val Asp Gln Val
                515                 520                 525

Ile Leu Ser Lys Asn Thr Ser Glu His Gly Gln Leu Asp Leu Leu Tyr
                530                 535                 540

Pro Ser Ile Asp Ser Glu Ser Glu Ile Leu Pro Gly Glu Asn Gln Val
545                 550                 555                 560

Phe Tyr Asp Asn Arg Thr Gln Asn Val Asp Tyr Leu Asn Ser Tyr Tyr
                565                 570                 575

Tyr Leu Glu Ser Gln Lys Leu Ser Asp Asn Val Glu Asp Phe Thr Phe
                580                 585                 590

Thr Arg Ser Ile Glu Glu Ala Leu Asp Asn Ser Ala Lys Val Tyr Thr
                595                 600                 605

Tyr Phe Pro Thr Leu Ala Asn Lys Val Asn Ala Gly Val Gln Gly Gly
                610                 615                 620

Leu Phe Leu Met Trp Ala Asn Asp Val Val Glu Asp Phe Thr Thr Asn
625                 630                 635                 640

Ile Leu Arg Lys Asp Thr Leu Asp Lys Ile Ser Asp Val Ser Ala Ile
                645                 650                 655

Ile Pro Tyr Ile Gly Pro Ala Leu Asn Ile Ser Asn Ser Val Arg Arg
                660                 665                 670

Gly Asn Phe Thr Glu Ala Phe Ala Val Thr Gly Val Thr Ile Leu Leu
                675                 680                 685

Glu Ala Phe Pro Glu Phe Thr Ile Pro Ala Leu Gly Ala Phe Val Ile
690                 695                 700

Tyr Ser Lys Val Gln Glu Arg Asn Glu Ile Ile Lys Thr Ile Asp Asn
705                 710                 715                 720

Cys Leu Glu Gln Arg Ile Lys Arg Trp Lys Asp Ser Tyr Glu Trp Met
                725                 730                 735

Met Gly Thr Trp Leu Ser Arg Ile Ile Thr Gln Phe Asn Asn Ile Ser
                740                 745                 750

Tyr Gln Met Tyr Asp Ser Leu Asn Tyr Gln Ala Gly Ala Ile Lys Ala
                755                 760                 765

Lys Ile Asp Leu Glu Tyr Lys Lys Tyr Ser Gly Ser Asp Lys Glu Asn
                770                 775                 780

Ile Lys Ser Gln Val Glu Asn Leu Lys Asn Ser Leu Asp Val Lys Ile
785                 790                 795                 800
```

```
Ser Glu Ala Met Asn Asn Ile Asn Lys Phe Ile Arg Glu Cys Ser Val
            805                 810                 815

Thr Tyr Leu Phe Lys Asn Met Leu Pro Lys Val Ile Asp Glu Leu Asn
        820                 825                 830

Glu Phe Asp Arg Asn Thr Lys Ala Lys Leu Ile Asn Leu Ile Asp Ser
            835                 840                 845

His Asn Ile Ile Leu Val Gly Glu Val Asp Lys Leu Lys Ala Lys Val
        850                 855                 860

Asn Asn Ser Phe Gln Asn Thr Ile Pro Phe Asn Ile Phe Ser Tyr Thr
865                 870                 875                 880

Asn Asn Ser Leu Leu Lys Asp Ile Ile Asn Glu Tyr Phe Asn Leu Glu
            885                 890                 895

Ala Leu Ala Ser Gly His His His His His His Lys Leu
        900                 905

<210> SEQ ID NO 25
<211> LENGTH: 213
<212> TYPE: DNA
<213> ORGANISM: artificial sequence
<220> FEATURE:
<223> OTHER INFORMATION: DNA sequence of the CP ANP-C linker

<400> SEQUENCE: 25
ggatccacgc acgtcgacgc gattgatggt cgttctctgc gtcgttcttc ttgcttcggt    60
ggtcgtatgg accgtatcgg tgctcagtct ggtctgggtt gcaactcttt ccgttacgcg   120
ctagcgggcg gtggcggtag cggcggtggc ggtagcggcg gtggcggtag cgcactagtg   180
ctgcagacgc acggtctaga atgataaaag ctt                                213

<210> SEQ ID NO 26
<211> LENGTH: 2790
<212> TYPE: DNA
<213> ORGANISM: artificial sequence
<220> FEATURE:
<223> OTHER INFORMATION: DNA sequence of the CP ANP-C fusion

<400> SEQUENCE: 26
ggatccgaat tcatgccgat caccatcaac aacttcaact acagcgatcc ggtggataac    60
aaaaacatcc tgtacctgga tacccatctg aatccctggc gaacgaaccc ggaaaaagcg   120
tttcgtatca ccggcaacat tgggttattc cggatcgttt tagccgtaaa cagcaacccg   180
aatctgaata aaccgccgcg tgttaccagc ccgaaaagcg gttattacga tccgaactat   240
ctgagcaccg atagcgataa agataccttc ctgaaagaaa tcatcaaact gttcaaacgc   300
atcaacagcc gtgaaattgg cgaagaactg atctatcgcc tgagcaccga tattccgttt   360
ccgggcaaca caacaccccc gatcaacacc tttgatttcg atgtggattt caacagcgtt   420
gatgttaaaa cccgccaggg taacaattgg gtgaaaaccg gcagcattaa cccgagcgtg   480
attattaccg gtccgcgcga aaacattatt gatccggaaa ccagcacctt taaactgacc   540
aacaacacct tgcggcgca ggaaggtttt ggcgcgctga gcattattag cattagcccg   600
cgctttatgc tgacctatag caacgcgacc aacgatgttg tgaaggccg tttcagcaaa   660 agcgaatttt gcatggaccc gatcctgatc ctgatgcatg aactgaacca tgcgatgcat   720
aacctgtatg gcatcgcgat tccgaacgat cagaccatta gcagcgtgac cagcaacatc   780
ttttacagcc agtacaacgt gaaactggaa tatgcggaaa tctatgcgtt ggcggtccg   840 accattgatc tgattccgaa aagcgcgcgc aaatacttcg aagaaaaagc gctggattac   900
tatcgcagca ttgcgaaacg tctgaacagc attaccaccg cgaatccgag cagcttcaac   960
```

```
aaatatatcg gcgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt ataccccggt gaccgcgaat attctggatg ataacgtgta cgatatccag    1200
aacggcttta acatcccgaa aagcaacctg aacgttctgt ttatgggcca gaacctgagc    1260
cgtaatccgg cgctgcgtaa agtgaacccg aaaacatgc tgtacctgtt caccaaattt     1320
tgcgtcgacg cgattgatgg tcgttctctg cgtcgttctt cttgcttcgg tggtcgtatg    1380
gaccgtatcg gtgctcagtc tggtctgggt tgcaactctt ccgttacgc gctagcgggc     1440 ggtggcggta gcggcggtgg cggtagcggc ggtggcggta gcgcactagt gctgcagtgt    1500
cgtgaactgc tggtgaaaaa caccgatctg ccgtttattg gcgatatcag cgatgtgaaa    1560
accgatatct tcctgcgcaa agatatcaac gaagaaaccg aagtgatcta ctacccggat    1620
aacgtgagcg ttgatcaggt gatcctgagc aaaaacacca gcaacatgg tcagctggat     1680 ctgctgtatc cgagcattga tagcgaaagc gaaattctgc cgggcgaaaa ccaggtgttt    1740
tacgataacc gtacccagaa cgtggattac ctgaacagct attactacct ggaaagccag    1800
aaactgagcg ataacgtgga agattttacc tttacccgca gcattgaaga agcgctggat    1860
aacagcgcga agtttacac ctattttccg accctggcga caaagttaa tgcgggtgtt      1920 cagggcggtc tgtttctgat gtgggcgaac gatgtggtgg aagatttcac caccaacatc    1980
ctgcgtaaag ataccctgga taaaatcagc gatgttagcg cgattattcc gtatattggt    2040
ccggcgctga acattagcaa tagcgtgcgt cgtggcaatt ttaccgaagc gtttgcggtt    2100
accggtgtga ccattctgct ggaagcgttt ccggaattta ccattccggc gctgggtgcg    2160
tttgtgatct atagcaaagt gcaggaacgc aacgaaatca tcaaaaccat cgataactgc    2220
ctggaacagc gtattaaacg ctggaaagat agctatgaat ggatgatggg cacctggctg    2280
agccgtatta tcacccagtt caacaacatc agctaccaga tgtacgatag cctgaactat    2340
caggcgggtg cgattaaagc gaaaatcgat ctggaataca aaaatacag cggcagcgat    2400 aaagaaaaca tcaaaagcca ggttgaaaac ctgaaaaaca gcctggatgt gaaaattagc    2460
gaagcgatga taacatcaa caaattcatc cgcgaatgca gcgtgaccta cctgttcaaa     2520
aacatgctgc gaaagtgat cgatgaactg aacgaatttg atcgcaacac caaagcgaaa     2580
ctgatcaacc tgatcgatag ccacaacatt attctggtgg cgaagtgga taaactgaaa     2640 gcgaaagtta acaacagctt ccagaacacc atcccgttta acatcttcag ctataccaac    2700
aacagcctgc tgaaagatat catcaacgaa tacttcaatc tagaagcact agcgagtggg    2760
caccatcacc atcaccatta atgaaagctt                                     2790
```

<210> SEQ ID NO 27  
<211> LENGTH: 928  
<212> TYPE: PRT  
<213> ORGANISM: artificial sequence  
<220> FEATURE:  
<223> OTHER INFORMATION: Protein sequence of the CP ANP-C fusion

<400> SEQUENCE: 27

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp

-continued

```
                35                  40                  45
Val Ile Pro Asp Arg Phe Ser Arg Asn Ser Asn Pro Asn Leu Asn Lys
 50                  55                  60
Pro Pro Arg Val Thr Ser Pro Lys Ser Gly Tyr Tyr Asp Pro Asn Tyr
 65                  70                  75                  80
Leu Ser Thr Asp Ser Asp Lys Asp Thr Phe Leu Lys Glu Ile Ile Lys
                 85                  90                  95
Leu Phe Lys Arg Ile Asn Ser Arg Glu Ile Gly Glu Leu Ile Tyr
                100                 105                 110
Arg Leu Ser Thr Asp Ile Pro Phe Pro Gly Asn Asn Asn Thr Pro Ile
                115                 120                 125
Asn Thr Phe Asp Phe Asp Val Asp Phe Asn Ser Val Asp Val Lys Thr
                130                 135                 140
Arg Gln Gly Asn Asn Trp Val Lys Thr Gly Ser Ile Asn Pro Ser Val
145                 150                 155                 160
Ile Ile Thr Gly Pro Arg Glu Asn Ile Ile Asp Pro Glu Thr Ser Thr
                165                 170                 175
Phe Lys Leu Thr Asn Asn Thr Phe Ala Ala Gln Glu Gly Phe Gly Ala
                180                 185                 190
Leu Ser Ile Ile Ser Ile Ser Pro Arg Phe Met Leu Thr Tyr Ser Asn
                195                 200                 205
Ala Thr Asn Asp Val Gly Glu Gly Arg Phe Ser Lys Ser Glu Phe Cys
                210                 215                 220
Met Asp Pro Ile Leu Ile Leu Met His Glu Leu Asn His Ala Met His
225                 230                 235                 240
Asn Leu Tyr Gly Ile Ala Ile Pro Asn Asp Gln Thr Ile Ser Ser Val
                245                 250                 255
Thr Ser Asn Ile Phe Tyr Ser Gln Tyr Asn Val Lys Leu Glu Tyr Ala
                260                 265                 270
Glu Ile Tyr Ala Phe Gly Gly Pro Thr Ile Asp Leu Ile Pro Lys Ser
                275                 280                 285
Ala Arg Lys Tyr Phe Glu Glu Lys Ala Leu Asp Tyr Tyr Arg Ser Ile
                290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                325                 330                 335
Val Val Glu Ser Ser Gly Glu Val Thr Val Asn Arg Asn Lys Phe Val
                340                 345                 350
Glu Leu Tyr Asn Glu Leu Thr Gln Ile Phe Thr Glu Phe Asn Tyr Ala
                355                 360                 365
Lys Ile Tyr Asn Val Gln Asn Arg Lys Ile Tyr Leu Ser Asn Val Tyr
                370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                405                 410                 415
Gln Asn Leu Ser Arg Asn Pro Ala Leu Arg Lys Val Asn Pro Glu Asn
                420                 425                 430
Met Leu Tyr Leu Phe Thr Lys Phe Cys Val Asp Ala Ile Asp Gly Arg
                435                 440                 445
Ser Leu Arg Arg Ser Ser Cys Phe Gly Gly Arg Met Asp Arg Ile Gly
                450                 455                 460
```

-continued

```
Ala Gln Ser Gly Leu Gly Cys Asn Ser Phe Arg Tyr Ala Leu Ala Gly
465                 470                 475                 480

Gly Gly Gly Ser Gly Gly Gly Ser Gly Gly Gly Ser Ala Leu
            485                 490                 495

Val Leu Gln Cys Arg Glu Leu Leu Val Lys Asn Thr Asp Leu Pro Phe
            500                 505                 510

Ile Gly Asp Ile Ser Asp Val Lys Thr Asp Ile Phe Leu Arg Lys Asp
            515                 520                 525

Ile Asn Glu Glu Thr Glu Val Ile Tyr Tyr Pro Asp Asn Val Ser Val
            530                 535                 540

Asp Gln Val Ile Leu Ser Lys Asn Thr Ser Glu His Gly Gln Leu Asp
545                 550                 555                 560

Leu Leu Tyr Pro Ser Ile Asp Ser Glu Ser Glu Ile Leu Pro Gly Glu
                565                 570                 575

Asn Gln Val Phe Tyr Asp Asn Arg Thr Gln Asn Val Asp Tyr Leu Asn
                580                 585                 590

Ser Tyr Tyr Tyr Leu Glu Ser Gln Lys Leu Ser Asp Asn Val Glu Asp
            595                 600                 605

Phe Thr Phe Thr Arg Ser Ile Glu Glu Ala Leu Asp Asn Ser Ala Lys
610                 615                 620

Val Tyr Thr Tyr Phe Pro Thr Leu Ala Asn Lys Val Asn Ala Gly Val
625                 630                 635                 640

Gln Gly Gly Leu Phe Leu Met Trp Ala Asn Asp Val Val Glu Asp Phe
                645                 650                 655

Thr Thr Asn Ile Leu Arg Lys Asp Thr Leu Asp Lys Ile Ser Asp Val
            660                 665                 670

Ser Ala Ile Ile Pro Tyr Ile Gly Pro Ala Leu Asn Ile Ser Asn Ser
            675                 680                 685

Val Arg Arg Gly Asn Phe Thr Glu Ala Phe Ala Val Thr Gly Val Thr
            690                 695                 700

Ile Leu Leu Glu Ala Phe Pro Glu Phe Thr Ile Pro Ala Leu Gly Ala
705                 710                 715                 720

Phe Val Ile Tyr Ser Lys Val Gln Glu Arg Asn Glu Ile Ile Lys Thr
                725                 730                 735

Ile Asp Asn Cys Leu Glu Gln Arg Ile Lys Arg Trp Lys Asp Ser Tyr
            740                 745                 750

Glu Trp Met Met Gly Thr Trp Leu Ser Arg Ile Ile Thr Gln Phe Asn
            755                 760                 765

Asn Ile Ser Tyr Gln Met Tyr Asp Ser Leu Asn Tyr Gln Ala Gly Ala
            770                 775                 780

Ile Lys Ala Lys Ile Asp Leu Glu Tyr Lys Lys Tyr Ser Gly Ser Asp
785                 790                 795                 800

Lys Glu Asn Ile Lys Ser Gln Val Glu Asn Leu Lys Asn Ser Leu Asp
                805                 810                 815

Val Lys Ile Ser Glu Ala Met Asn Asn Ile Asn Lys Phe Ile Arg Glu
            820                 825                 830

Cys Ser Val Thr Tyr Leu Phe Lys Asn Met Leu Pro Lys Val Ile Asp
            835                 840                 845

Glu Leu Asn Glu Phe Asp Arg Asn Thr Lys Ala Lys Leu Ile Asn Leu
850                 855                 860

Ile Asp Ser His Asn Ile Ile Leu Val Gly Glu Val Asp Lys Leu Lys
865                 870                 875                 880

Ala Lys Val Asn Asn Ser Phe Gln Asn Thr Ile Pro Phe Asn Ile Phe
                885                 890                 895
```

```
Ser Tyr Thr Asn Asn Ser Leu Leu Lys Asp Ile Ile Asn Glu Tyr Phe
                900                 905                 910

Asn Leu Glu Ala Leu Ala Ser Gly His His His His His His Lys Leu
        915                 920                 925

<210> SEQ ID NO 28
<211> LENGTH: 213
<212> TYPE: DNA
<213> ORGANISM: artificial sequence
<220> FEATURE:
<223> OTHER INFORMATION: DNA sequence of the CP VIP-C linker

<400> SEQUENCE: 28
ggatccacgc acgtcgacgc gattgatggt cgtcactctg acgctgtttt caccgacaac      60
tacacccgtc tgcgtaaaca gatggctgtt aaaaaatacc tgaactctat cctgaacgcg     120
ctagcgggcg gtggcggtag cggcggtggc ggtagcggcg gtggcggtag cgcactagtg     180
ctgcagacgc acggtctaga atgataaaag ctt                                  213

<210> SEQ ID NO 29
<211> LENGTH: 2730
<212> TYPE: DNA
<213> ORGANISM: artificial sequence
<220> FEATURE:
<223> OTHER INFORMATION: DNA sequence of the CP VIP-C fusion

<400> SEQUENCE: 29
aaaaacatcc tgtacctgga tacccatctg aatccctggc gaacgaacc ggaaaaagcg       60 tttcgtatca ccggcaacat ttgggttatt ccggatcgtt ttagccgtaa cagcaaccecg    120 aatctgaata aaccgccgcg tgttaccagc ccgaaaagcg gttattacga tccgaactat    180
ctgagcaccg atagcgataa agataccttc ctgaaagaaa tcatcaaact gttcaaacgc    240
atcaacagcc gtgaaattgg cgaagaactg atctatcgcc tgagcaccga tattccgttt    300
ccgggcaaca caacaccccc gatcaacacc tttgatttcg atgtggattt caacagcgtt    360
gatgttaaaa cccgccaggg taacaattgg gtgaaaaccg gcagcattaa cccgagcgtg    420
attattaccg gtccgcgcga aaacattatt gatccggaaa ccagcacctt taaactgacc    480
aacaacacct tgcggcgca ggaaggtttt ggcgcgctga gcattattag cattagcccg    540
cgctttatgc tgacctatag caacgcgacc aacgatgttg gtgaaggccg tttcagcaaa    600
agcgaatttt gcatggaccc gatcctgatc ctgatgcatg aactgaacca tgcgatgcat    660
aacctgtatg gcatcgcgat ccgaacgat cagaccatta gcagcgtgac cagcaacatc    720 tttacagcc agtacaacgt gaaactggaa tatgcgaaa ctatgcgtt tggcggtccg    780 accattgatc tgattccgaa agcgcgcgc aaatacttcg aagaaaaagc gctggattac    840
tatcgcagca ttgcgaaacg tctgaacagc attaccaccg cgaatccgag cagcttcaac    900
aaatatatcg gcgaatataa acagaaactg atccgcaaat atcgctttgt ggtggaaagc    960
agcggcgaag ttaccgttaa ccgcaataaa ttcgtggaac tgtacaacga actgaccccag   1020 atcttcaccg aatttaacta tgcgaaaatc tataacgtgc agaaccgtaa aatctacctg   1080
agcaacgtgt ataccccggt gaccgcgaat attctggatg ataacgtgta cgatatccag   1140
aacggcttta acatcccgaa aagcaacctg aacgttctgt tatgggcca gaacctgagc   1200 cgtaatccgg cgctgcgtaa agtgaacccg gaaaacatgc tgtacctgtt caccaaattt   1260
tgcgtcgacg cgattgatgg tcgtggtggt cgtggtgaca tgttcggtgc tgcgctagcg   1320
ggcgtcgacg cgattgatgg tcgtcactct gacgctgttt tcaccgacaa ctacacccgt   1380
```

```
ctgcgtaaac agatggctgt taaaaaatac ctgaactcta tcctgaacgc gctagcgggc   1440
ggtggcggta gcggcggtgg cggtagcggc ggtggcggta gcgcactagt gctgcagaaa   1500
accgatatct tcctgcgcaa agatatcaac gaagaaaccg aagtgatcta ctacccggat   1560
aacgtgagcg ttgatcaggt gatcctgagc aaaaacacca gcgaacatgg tcagctggat   1620
ctgctgtatc cgagcattga tagcgaaagc gaaattctgc cgggcgaaaa ccaggtgttt   1680
tacgataacc gtacccagaa cgtggattac ctgaacagct attactacct ggaaagccag   1740
aaactgagcg ataacgtgga agattttacc tttacccgca gcattgaaga agcgctggat   1800
aacagcgcga aagtttacac ctattttccg accctggcga caaagttaa tgcgggtgtt   1860 cagggcggtc tgtttctgat gtgggcgaac gatgtggtgg aagatttcac caccaacatc   1920
ctgcgtaaag ataccctgga taaaatcagc gatgttagcg cgattattcc gtatattggt   1980
ccggcgctga acattagcaa tagcgtgcgt cgtggcaatt ttaccgaagc gtttgcggtt   2040
accggtgtga ccattctgct ggaagcgttt ccggaattta ccattccggc gctgggtgcg   2100
tttgtgatct atagcaaagt gcaggaacgc aacgaaatca tcaaaaccat cgataactgc   2160
ctggaacagc gtattaaacg ctggaaagat agctatgaat ggatgatggg cacctggctg   2220
agccgtatta tcacccagtt caacaacatc agctaccaga tgtacgatag cctgaactat   2280
caggcgggtg cgattaaagc gaaaatcgat ctggaataca aaaaatacag cggcagcgat   2340
aaagaaaaca tcaaaagcca ggttgaaaac ctgaaaaaca gcctggatgt gaaaattagc   2400
gaagcgatga taacatcaa caattcatc cgcgaatgca gcgtgaccta cctgttcaaa   2460
aacatgctgc cgaaagtgat cgatgaactg aacgaatttg atcgcaacac caaagcgaaa   2520
ctgatcaacc tgatcgatag ccacaacatt attctggtgg cgaagtgga taaactgaaa   2580 gcgaaagtta acaacagctt ccagaacacc atcccgttta acatcttcag ctataccaac   2640
aacagcctgc tgaaagatat catcaacgaa tacttcaatc tagaagcact agcgagtggg   2700
caccatcacc atcaccatta atgaaagctt                                   2730
```

<210> SEQ ID NO 30
<211> LENGTH: 908
<212> TYPE: PRT
<213> ORGANISM: artificial sequence
<220> FEATURE:
<223> OTHER INFORMATION: Protein sequence of the CP VIP-C fusion

<400> SEQUENCE: 30

```
Lys Asn Ile Leu Tyr Leu Asp Thr His Leu Asn Thr Leu Ala Asn Glu
1               5                   10                  15

Pro Glu Lys Ala Phe Arg Ile Thr Gly Asn Ile Trp Val Ile Pro Asp
            20                  25                  30

Arg Phe Ser Arg Asn Ser Asn Pro Asn Leu Asn Lys Pro Pro Arg Val
        35                  40                  45

Thr Ser Pro Lys Ser Gly Tyr Tyr Asp Pro Asn Tyr Leu Ser Thr Asp
    50                  55                  60

Ser Asp Lys Asp Thr Phe Leu Lys Glu Ile Ile Lys Leu Phe Lys Arg
65                  70                  75                  80

Ile Asn Ser Arg Glu Ile Gly Glu Glu Leu Ile Tyr Arg Leu Ser Thr
                85                  90                  95

Asp Ile Pro Phe Pro Gly Asn Asn Asn Thr Pro Ile Asn Thr Phe Asp
            100                 105                 110

Phe Asp Val Asp Phe Asn Ser Val Asp Val Lys Thr Arg Gln Gly Asn
        115                 120                 125
```

```
Asn Trp Val Lys Thr Gly Ser Ile Asn Pro Ser Val Ile Thr Gly
    130                 135                 140

Pro Arg Glu Asn Ile Ile Asp Pro Glu Thr Ser Thr Phe Lys Leu Thr
145                 150                 155                 160

Asn Asn Thr Phe Ala Ala Gln Glu Gly Phe Gly Ala Leu Ser Ile Ile
                165                 170                 175

Ser Ile Ser Pro Arg Phe Met Leu Thr Tyr Ser Asn Ala Thr Asn Asp
            180                 185                 190

Val Gly Glu Gly Arg Phe Ser Lys Ser Glu Phe Cys Met Asp Pro Ile
        195                 200                 205

Leu Ile Leu Met His Glu Leu Asn His Ala Met His Asn Leu Tyr Gly
    210                 215                 220

Ile Ala Ile Pro Asn Asp Gln Thr Ile Ser Ser Val Thr Ser Asn Ile
225                 230                 235                 240

Phe Tyr Ser Gln Tyr Asn Val Lys Leu Glu Tyr Ala Glu Ile Tyr Ala
                245                 250                 255

Phe Gly Gly Pro Thr Ile Asp Leu Ile Pro Lys Ser Ala Arg Lys Tyr
            260                 265                 270

Phe Glu Glu Lys Ala Leu Asp Tyr Tyr Arg Ser Ile Ala Lys Arg Leu
        275                 280                 285

Asn Ser Ile Thr Thr Ala Asn Pro Ser Ser Phe Asn Lys Tyr Ile Gly
290                 295                 300

Glu Tyr Lys Gln Lys Leu Ile Arg Lys Tyr Arg Phe Val Val Glu Ser
305                 310                 315                 320

Ser Gly Glu Val Thr Val Asn Arg Asn Lys Phe Val Glu Leu Tyr Asn
                325                 330                 335

Glu Leu Thr Gln Ile Phe Thr Glu Phe Asn Tyr Ala Lys Ile Tyr Asn
            340                 345                 350

Val Gln Asn Arg Lys Ile Tyr Leu Ser Asn Val Tyr Thr Pro Val Thr
        355                 360                 365

Ala Asn Ile Leu Asp Asp Asn Val Tyr Asp Ile Gln Asn Gly Phe Asn
    370                 375                 380

Ile Pro Lys Ser Asn Leu Asn Val Leu Phe Met Gly Gln Asn Leu Ser
385                 390                 395                 400

Arg Asn Pro Ala Leu Arg Lys Val Asn Pro Glu Asn Met Leu Tyr Leu
                405                 410                 415

Phe Thr Lys Phe Cys Val Asp Ala Ile Asp Gly Arg Gly Arg Gly
            420                 425                 430

Asp Met Phe Gly Ala Ala Leu Ala Gly Val Asp Ala Ile Asp Gly Arg
        435                 440                 445

His Ser Asp Ala Val Phe Thr Asp Asn Tyr Thr Arg Leu Arg Lys Gln
    450                 455                 460

Met Ala Val Lys Lys Tyr Leu Asn Ser Ile Leu Asn Ala Leu Ala Gly
465                 470                 475                 480

Gly Gly Gly Ser Gly Gly Gly Ser Gly Gly Gly Ser Ala Leu
                485                 490                 495

Val Leu Gln Lys Thr Asp Ile Phe Leu Arg Lys Asp Ile Asn Glu Glu
            500                 505                 510

Thr Glu Val Ile Tyr Tyr Pro Asp Asn Val Ser Val Asp Gln Val Ile
        515                 520                 525

Leu Ser Lys Asn Thr Ser Glu His Gly Gln Leu Asp Leu Leu Tyr Pro
    530                 535                 540

Ser Ile Asp Ser Glu Ser Glu Ile Leu Pro Gly Glu Asn Gln Val Phe
```

```
                    545                 550                 555                 560
Tyr Asp Asn Arg Thr Gln Asn Val Asp Tyr Leu Asn Ser Tyr Tyr Tyr
                565                 570                 575
Leu Glu Ser Gln Lys Leu Ser Asp Asn Val Glu Asp Phe Thr Phe Thr
                580                 585                 590
Arg Ser Ile Glu Glu Ala Leu Asp Asn Ser Ala Lys Val Tyr Thr Tyr
                595                 600                 605
Phe Pro Thr Leu Ala Asn Lys Val Asn Ala Gly Val Gln Gly Gly Leu
                610                 615                 620
Phe Leu Met Trp Ala Asn Asp Val Val Glu Asp Phe Thr Thr Asn Ile
625                 630                 635                 640
Leu Arg Lys Asp Thr Leu Asp Lys Ile Ser Asp Val Ser Ala Ile Ile
                645                 650                 655
Pro Tyr Ile Gly Pro Ala Leu Asn Ile Ser Asn Ser Val Arg Arg Gly
                660                 665                 670
Asn Phe Thr Glu Ala Phe Ala Val Thr Gly Val Thr Ile Leu Leu Glu
                675                 680                 685
Ala Phe Pro Glu Phe Thr Ile Pro Ala Leu Gly Ala Phe Val Ile Tyr
                690                 695                 700
Ser Lys Val Gln Glu Arg Asn Glu Ile Ile Lys Thr Ile Asp Asn Cys
705                 710                 715                 720
Leu Glu Gln Arg Ile Lys Arg Trp Lys Asp Ser Tyr Glu Trp Met Met
                725                 730                 735
Gly Thr Trp Leu Ser Arg Ile Ile Thr Gln Phe Asn Asn Ile Ser Tyr
                740                 745                 750
Gln Met Tyr Asp Ser Leu Asn Tyr Gln Ala Gly Ala Ile Lys Ala Lys
                755                 760                 765
Ile Asp Leu Glu Tyr Lys Lys Tyr Ser Gly Ser Asp Lys Glu Asn Ile
770                 775                 780
Lys Ser Gln Val Glu Asn Leu Lys Asn Ser Leu Asp Val Lys Ile Ser
785                 790                 795                 800
Glu Ala Met Asn Asn Ile Asn Lys Phe Ile Arg Glu Cys Ser Val Thr
                805                 810                 815
Tyr Leu Phe Lys Asn Met Leu Pro Lys Val Ile Asp Glu Leu Asn Glu
                820                 825                 830
Phe Asp Arg Asn Thr Lys Ala Lys Leu Ile Asn Leu Ile Asp Ser His
                835                 840                 845
Asn Ile Ile Leu Val Gly Glu Val Asp Lys Leu Lys Ala Lys Val Asn
850                 855                 860
Asn Ser Phe Gln Asn Thr Ile Pro Phe Asn Ile Phe Ser Tyr Thr Asn
865                 870                 875                 880
Asn Ser Leu Leu Lys Asp Ile Ile Asn Glu Tyr Phe Asn Leu Glu Ala
                885                 890                 895
Leu Ala Ser Gly His His His His His His Lys Leu
                900                 905
```

<210> SEQ ID NO 31
<211> LENGTH: 210
<212> TYPE: DNA
<213> ORGANISM: artificial sequence
<220> FEATURE:
<223> OTHER INFORMATION: DNA sequecne of the CP Gastrin releasing peptide -C linker

<400> SEQUENCE: 31
ggatccacgc acgtcgacgc gattgatggt cgtgttccgc tgccggctgg tggtggtacc        60

```
gttctgacca aaatgtaccc gcgtggtaac cactgggctg ttggtcacct gatggcgcta    120
gcgggcggtg gcggtagcgg cggtggcggt agcggcggtg gcggtagcgc actagtgctg    180
cagacgcacg gtctagaatg ataaaagctt                                     210
```

<210> SEQ ID NO 32
<211> LENGTH: 2787
<212> TYPE: DNA
<213> ORGANISM: artificial sequence
<220> FEATURE:
<223> OTHER INFORMATION: DNA sequence of the CP Gastrin releasing peptide -C fusion

<400> SEQUENCE: 32

```
ggatccgaat tcatgccgat caccatcaac aacttcaact acagcgatcc ggtggataac     60
aaaaacatcc tgtacctgga tacccatctg aatccctggc gaacgaacc ggaaaaagcg    120 tttcgtatca ccggcaacat tgggttatt ccggatcgtt ttagccgtaa cagcaacccg    180
aatctgaata accgccgcg tgttaccagc ccgaaaagcg gttattacga tccgaactat    240
ctgagcaccg atagcgataa agatacccttc tgaaagaaa tcatcaaact gttcaaacgc    300
atcaacagcc gtgaaattgg cgaagaactg atctatcgcc tgagcaccga tattccgttt    360
ccgggcaaca caacaccccc gatcaacacc tttgatttcg atgtggattt caacagcgtt    420
gatgttaaaa cccgccaggg taacaattgg gtgaaaaccg gcagcattaa cccgagcgtg    480
attattaccg gtccgcgcga aaacattatt gatccggaaa ccagcacctt taaactgacc    540
aacaacacct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg cgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt ataccccggt gaccgcgaat attctggatg ataacgtgta cgatatccag    1200 aacggctttta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg cgattgatgg tcgtgttccg ctgccggctg gtggtggtac cgttctgacc    1380
aaaatgtacc cgcgtggtaa ccactgggct gttggtcacc tgatggcgct agcgggcggt    1440
ggcggtagcg gcggtggcgg tagcggcggt ggcggtagcg cactagtgct gcagtgtcgt    1500
gaactgctgg tgaaaaacac cgatctgccg tttattggcg atatcagcga tgtgaaaacc    1560
gatatcttcc tgcgcaaaga tatcaacgaa gaaaccgaag tgatctacta cccggataac    1620
gtgagcgttg atcaggtgat cctgagcaaa acaccagcg aacatggtca gctggatctg    1680
ctgtatccga gcattgatag cgaaagcgaa attctgccgg gcgaaaacca ggtgttttac    1740
gataaccgta cccagaacgt ggattacctg aacagctatt actacctgga aagccagaaa    1800
ctgagcgata acgtggaaga ttttacccttt acccgcagca ttgaagaagc gctggataac    1860
```

-continued agcgcgaaag tttacaccta ttttccgacc ctggcgaaca aagttaatgc gggtgttcag 1920
ggcggtctgt ttctgatgtg ggcgaacgat gtggtggaag atttcaccac caacatcctg 1980
cgtaaagata ccctggataa aatcagcgat gttagcgcga ttattccgta tattggtccg 2040
gcgctgaaca ttagcaatag cgtgcgtcgt ggcaatttta ccgaagcgtt tgcggttacc 2100
ggtgtgacca ttctgctgga agcgtttccg gaatttacca ttccggcgct gggtgcgttt 2160
gtgatctata gcaaagtgca ggaacgcaac gaaatcatca aaaccatcga taactgcctg 2220
gaacagcgta ttaaacgctg gaaagatagc tatgaatgga tgatgggcac ctggctgagc 2280
cgtattatca cccagttcaa caacatcagc taccagatgt acgatagcct gaactatcag 2340
gcgggtgcga ttaaagcgaa aatcgatctg gaatacaaaa aatacagcgg cagcgataaa 2400
gaaaacatca aaagccaggt tgaaaacctg aaaaacagcc tggatgtgaa aattagcgaa 2460
gcgatgaata acatcaacaa attcatccgc gaatgcagcg tgacctacct gttcaaaaac 2520
atgctgccga aagtgatcga tgaactgaac gaatttgatc gcaacaccaa agcgaaactg 2580
atcaacctga tcgatagcca caacattatt ctggtgggcg aagtggataa actgaaagcg 2640
aaagttaaca acagcttcca gaacaccatc ccgtttaaca tcttcagcta taccaacaac 2700
agcctgctga aagatatcat caacgaatac ttcaatctag aagcactagc gagtgggcac 2760
catcaccatc accattaatg aaagctt 2787

<210> SEQ ID NO 33
<211> LENGTH: 927
<212> TYPE: PRT
<213> ORGANISM: artificial sequence
<220> FEATURE:
<223> OTHER INFORMATION: Protein sequence of the CP Gastrin releasing peptide -C fusion

<400> SEQUENCE: 33

Gly Ser Glu Phe Met Pro Ile Thr Ile Asn Asn Phe Asn Tyr Ser Asp
1 5 10 15

Pro Val Asp Asn Lys Asn Ile Leu Tyr Leu Asp Thr His Leu Asn Thr
20 25 30

Leu Ala Asn Glu Pro Glu Lys Ala Phe Arg Ile Thr Gly Asn Ile Trp
35 40 45

Val Ile Pro Asp Arg Phe Ser Arg Asn Ser Asn Pro Asn Leu Asn Lys
50 55 60

Pro Pro Arg Val Thr Ser Pro Lys Ser Gly Tyr Tyr Asp Pro Asn Tyr
65 70 75 80

Leu Ser Thr Asp Ser Asp Lys Asp Thr Phe Leu Lys Glu Ile Ile Lys
85 90 95

Leu Phe Lys Arg Ile Asn Ser Arg Glu Ile Gly Glu Glu Leu Ile Tyr
100 105 110

Arg Leu Ser Thr Asp Ile Pro Phe Pro Gly Asn Asn Asn Thr Pro Ile
115 120 125

Asn Thr Phe Asp Phe Asp Val Asp Phe Asn Ser Val Asp Val Lys Thr
130 135 140

Arg Gln Gly Asn Asn Trp Val Lys Thr Gly Ser Ile Asn Pro Ser Val
145 150 155 160

Ile Ile Thr Gly Pro Arg Glu Asn Ile Ile Asp Pro Glu Thr Ser Thr
165 170 175

Phe Lys Leu Thr Asn Asn Thr Phe Ala Ala Gln Glu Gly Phe Gly Ala
180 185 190

Leu Ser Ile Ile Ser Ile Ser Pro Arg Phe Met Leu Thr Tyr Ser Asn

```
            195                 200                 205
Ala Thr Asn Asp Val Gly Glu Gly Arg Phe Ser Lys Ser Glu Phe Cys
210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
                260                 265                 270

Glu Ile Tyr Ala Phe Gly Gly Pro Thr Ile Asp Leu Ile Pro Lys Ser
                275                 280                 285

Ala Arg Lys Tyr Phe Glu Glu Lys Ala Leu Asp Tyr Tyr Arg Ser Ile
290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
                340                 345                 350

Glu Leu Tyr Asn Glu Leu Thr Gln Ile Phe Thr Glu Phe Asn Tyr Ala
                355                 360                 365

Lys Ile Tyr Asn Val Gln Asn Arg Lys Ile Tyr Leu Ser Asn Val Tyr
                370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
                420                 425                 430

Met Leu Tyr Leu Phe Thr Lys Phe Cys Val Asp Ala Ile Asp Gly Arg
                435                 440                 445

Val Pro Leu Pro Ala Gly Gly Thr Val Leu Thr Lys Met Tyr Pro
450                 455                 460

Arg Gly Asn His Trp Ala Val Gly His Leu Met Ala Leu Ala Gly Gly
465                 470                 475                 480

Gly Gly Ser Gly Gly Gly Ser Gly Gly Gly Ser Ala Leu Val
                485                 490                 495

Leu Gln Cys Arg Glu Leu Leu Val Lys Asn Thr Asp Leu Pro Phe Ile
                500                 505                 510

Gly Asp Ile Ser Asp Val Lys Thr Asp Ile Phe Leu Arg Lys Asp Ile
                515                 520                 525

Asn Glu Glu Thr Glu Val Ile Tyr Tyr Pro Asp Asn Val Ser Val Asp
530                 535                 540

Gln Val Ile Leu Ser Lys Asn Thr Ser Glu His Gly Gln Leu Asp Leu
545                 550                 555                 560

Leu Tyr Pro Ser Ile Asp Ser Glu Ser Glu Ile Leu Pro Gly Glu Asn
                565                 570                 575

Gln Val Phe Tyr Asp Asn Arg Thr Gln Asn Val Asp Tyr Leu Asn Ser
                580                 585                 590

Tyr Tyr Tyr Leu Glu Ser Gln Lys Leu Ser Asp Asn Val Glu Asp Phe
                595                 600                 605

Thr Phe Thr Arg Ser Ile Glu Glu Ala Leu Asp Asn Ser Ala Lys Val
610                 615                 620
```

```
Tyr Thr Tyr Phe Pro Thr Leu Ala Asn Lys Val Asn Ala Gly Val Gln
625                 630                 635                 640

Gly Gly Leu Phe Leu Met Trp Ala Asn Asp Val Val Glu Asp Phe Thr
            645                 650                 655

Thr Asn Ile Leu Arg Lys Asp Thr Leu Asp Lys Ile Ser Asp Val Ser
        660                 665                 670

Ala Ile Ile Pro Tyr Ile Gly Pro Ala Leu Asn Ile Ser Asn Ser Val
    675                 680                 685

Arg Arg Gly Asn Phe Thr Glu Ala Phe Ala Val Thr Gly Val Thr Ile
690                 695                 700

Leu Leu Glu Ala Phe Pro Glu Phe Thr Ile Pro Ala Leu Gly Ala Phe
705                 710                 715                 720

Val Ile Tyr Ser Lys Val Gln Glu Arg Asn Glu Ile Ile Lys Thr Ile
            725                 730                 735

Asp Asn Cys Leu Glu Gln Arg Ile Lys Arg Trp Lys Asp Ser Tyr Glu
        740                 745                 750

Trp Met Met Gly Thr Trp Leu Ser Arg Ile Ile Thr Gln Phe Asn Asn
    755                 760                 765

Ile Ser Tyr Gln Met Tyr Asp Ser Leu Asn Tyr Gln Ala Gly Ala Ile
770                 775                 780

Lys Ala Lys Ile Asp Leu Glu Tyr Lys Tyr Ser Gly Ser Asp Lys
785                 790                 795                 800

Glu Asn Ile Lys Ser Gln Val Glu Asn Leu Lys Asn Ser Leu Asp Val
            805                 810                 815

Lys Ile Ser Glu Ala Met Asn Asn Ile Asn Lys Phe Ile Arg Glu Cys
        820                 825                 830

Ser Val Thr Tyr Leu Phe Lys Asn Met Leu Pro Lys Val Ile Asp Glu
    835                 840                 845

Leu Asn Glu Phe Asp Arg Asn Thr Lys Ala Lys Leu Ile Asn Leu Ile
850                 855                 860

Asp Ser His Asn Ile Ile Leu Val Gly Glu Val Asp Lys Leu Lys Ala
865                 870                 875                 880

Lys Val Asn Asn Ser Phe Gln Asn Thr Ile Pro Phe Asn Ile Phe Ser
            885                 890                 895

Tyr Thr Asn Asn Ser Leu Leu Lys Asp Ile Ile Asn Glu Tyr Phe Asn
        900                 905                 910

Leu Glu Ala Leu Ala Ser Gly His His His His His Lys Leu
            915                 920                 925

<210> SEQ ID NO 34
<211> LENGTH: 10
<212> TYPE: PRT
<213> ORGANISM: artificial sequence
<220> FEATURE:
<223> OTHER INFORMATION: synthetic peptide

<400> SEQUENCE: 34

Pro Leu Ala Glu Ile Asp Gly Ile Glu Leu
1               5                   10

<210> SEQ ID NO 35
<211> LENGTH: 12
<212> TYPE: PRT
<213> ORGANISM: artificial sequence
<220> FEATURE:
<223> OTHER INFORMATION: synthetic peptide

<400> SEQUENCE: 35
```

```
Cys Pro Leu Ala Glu Ile Asp Gly Ile Glu Leu Cys
1               5                   10

<210> SEQ ID NO 36
<211> LENGTH: 7
<212> TYPE: PRT
<213> ORGANISM: artificial sequence
<220> FEATURE:
<223> OTHER INFORMATION: synthetic peptide

<400> SEQUENCE: 36

Thr His Ala Leu Trp His Thr
1               5

<210> SEQ ID NO 37
<211> LENGTH: 15
<212> TYPE: PRT
<213> ORGANISM: artificial sequence
<220> FEATURE:
<223> OTHER INFORMATION: LEBP-1 peptide

<400> SEQUENCE: 37

Gln Pro Phe Met Gln Cys Leu Cys Leu Ile Tyr Asp Ala Ser Cys
1               5                   10                  15

<210> SEQ ID NO 38
<211> LENGTH: 15
<212> TYPE: PRT
<213> ORGANISM: artificial sequence
<220> FEATURE:
<223> OTHER INFORMATION: LEBP-2 peptide

<400> SEQUENCE: 38

Arg Asn Val Pro Pro Ile Phe Asn Asp Val Tyr Trp Ile Ala Phe
1               5                   10                  15

<210> SEQ ID NO 39
<211> LENGTH: 14
<212> TYPE: PRT
<213> ORGANISM: artificial sequence
<220> FEATURE:
<223> OTHER INFORMATION: LEBP-3 peptide

<400> SEQUENCE: 39

Val Phe Arg Val Arg Pro Trp Tyr Gln Ser Thr Ser Gln Ser
1               5                   10

<210> SEQ ID NO 40
<211> LENGTH: 7
<212> TYPE: PRT
<213> ORGANISM: artificial sequence
<220> FEATURE:
<223> OTHER INFORMATION: sythetic peptide

<400> SEQUENCE: 40

Ser Glu Arg Ser Met Asn Phe
1               5

<210> SEQ ID NO 41
<211> LENGTH: 7
<212> TYPE: PRT
<213> ORGANISM: artificial sequence
<220> FEATURE:
<223> OTHER INFORMATION: synthetic peptide

<400> SEQUENCE: 41

Tyr Gly Leu Pro His Lys Phe
1               5
```

<210> SEQ ID NO 42
<211> LENGTH: 7
<212> TYPE: PRT
<213> ORGANISM: artificial sequence
<220> FEATURE:
<223> OTHER INFORMATION: synthetic peptide

<400> SEQUENCE: 42

Pro Ser Gly Ala Ala Arg Ala
1               5

<210> SEQ ID NO 43
<211> LENGTH: 7
<212> TYPE: PRT
<213> ORGANISM: artificial sequence
<220> FEATURE:
<223> OTHER INFORMATION: synthetic peptide

<400> SEQUENCE: 43

Leu Pro His Lys Ser Met Pro
1               5

<210> SEQ ID NO 44
<211> LENGTH: 7
<212> TYPE: PRT
<213> ORGANISM: artificial sequence
<220> FEATURE:
<223> OTHER INFORMATION: synthetic peptide

<400> SEQUENCE: 44

Leu Gln His Lys Ser Met Pro
1               5

<210> SEQ ID NO 45
<211> LENGTH: 7
<212> TYPE: PRT
<213> ORGANISM: artificial sequence
<220> FEATURE:
<223> OTHER INFORMATION: synthetic peptide

<400> SEQUENCE: 45

Phe Ser Leu Ser Lys Pro Pro
1               5

<210> SEQ ID NO 46
<211> LENGTH: 7
<212> TYPE: PRT
<213> ORGANISM: artificial sequence
<220> FEATURE:
<223> OTHER INFORMATION: synthetic peptide

<400> SEQUENCE: 46

His Ser Met Gln Leu Ser Thr
1               5

<210> SEQ ID NO 47
<211> LENGTH: 7
<212> TYPE: PRT
<213> ORGANISM: artificial sequence
<220> FEATURE:
<223> OTHER INFORMATION: synthetic peptide

<400> SEQUENCE: 47

Ser Thr Gln Ala Met Phe Gln
1               5

```
<210> SEQ ID NO 48
<211> LENGTH: 17
<212> TYPE: PRT
<213> ORGANISM: artificial sequence
<220> FEATURE:
<223> OTHER INFORMATION: synthetic peptide

<400> SEQUENCE: 48

Cys Asp Ser Ala Phe Val Thr Val Asp Trp Gly Arg Ser Met Ser Leu
1               5                   10                  15

Cys

<210> SEQ ID NO 49
<211> LENGTH: 5
<212> TYPE: PRT
<213> ORGANISM: artificial sequence
<220> FEATURE:
<223> OTHER INFORMATION: synthetic peptide

<400> SEQUENCE: 49

Asp Asp Asp Asp Lys
1               5

<210> SEQ ID NO 50
<211> LENGTH: 4
<212> TYPE: PRT
<213> ORGANISM: artificial sequence
<220> FEATURE:
<223> OTHER INFORMATION: synthetic peptide

<400> SEQUENCE: 50

Ile Glu Gly Arg
1

<210> SEQ ID NO 51
<211> LENGTH: 4
<212> TYPE: PRT
<213> ORGANISM: artificial sequence
<220> FEATURE:
<223> OTHER INFORMATION: synthetic peptide

<400> SEQUENCE: 51

Ile Asp Gly Arg
1

<210> SEQ ID NO 52
<211> LENGTH: 7
<212> TYPE: PRT
<213> ORGANISM: artificial sequence
<220> FEATURE:
<223> OTHER INFORMATION: synthetic peptide

<400> SEQUENCE: 52

Glu Asn Leu Tyr Phe Gln Gly
1               5

<210> SEQ ID NO 53
<211> LENGTH: 6
<212> TYPE: PRT
<213> ORGANISM: artificial sequence
<220> FEATURE:
<223> OTHER INFORMATION: synthetic peptide

<400> SEQUENCE: 53

Leu Val Pro Arg Gly Ser
1               5
```

```
<210> SEQ ID NO 54
<211> LENGTH: 8
<212> TYPE: PRT
<213> ORGANISM: artificial sequence
<220> FEATURE:
<223> OTHER INFORMATION: synthetic peptide

<400> SEQUENCE: 54

Leu Glu Val Leu Phe Gln Gly Pro
1               5

<210> SEQ ID NO 55
<211> LENGTH: 25
<212> TYPE: PRT
<213> ORGANISM: Clostridium Botulinum
<220> FEATURE:
<223> OTHER INFORMATION: Type A1

<400> SEQUENCE: 55

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 56
<211> LENGTH: 25
<212> TYPE: PRT
<213> ORGANISM: Clostridium Botulinum
<220> FEATURE:
<223> OTHER INFORMATION: Type A2

<400> SEQUENCE: 56

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 57
<211> LENGTH: 10
<212> TYPE: PRT
<213> ORGANISM: Clostridium Botulinum
<220> FEATURE:
<223> OTHER INFORMATION: Type B

<400> SEQUENCE: 57

Cys Lys Ser Val Lys Ala Pro Gly Ile Cys
1               5                   10

<210> SEQ ID NO 58
<211> LENGTH: 17
<212> TYPE: PRT
<213> ORGANISM: Clostridium Botulinum
<220> FEATURE:
<223> OTHER INFORMATION: Type C

<400> SEQUENCE: 58

Cys His Lys Ala Ile Asp Gly Arg Ser Leu Tyr Asn Lys Thr Leu Asp
1               5                   10                  15

Cys

<210> SEQ ID NO 59
<211> LENGTH: 14
<212> TYPE: PRT
<213> ORGANISM: Clostridium Botulinum
<220> FEATURE:
<223> OTHER INFORMATION: Type D
```

```
<400> SEQUENCE: 59

Cys Leu Arg Leu Thr Lys Asn Ser Arg Asp Asp Ser Thr Cys
1               5                   10

<210> SEQ ID NO 60
<211> LENGTH: 15
<212> TYPE: PRT
<213> ORGANISM: Clostridium Botulinum
<220> FEATURE:
<223> OTHER INFORMATION: Type E

<400> SEQUENCE: 60

Cys Lys Asn Ile Val Ser Val Lys Gly Ile Arg Lys Ser Ile Cys
1               5                   10                  15

<210> SEQ ID NO 61
<211> LENGTH: 17
<212> TYPE: PRT
<213> ORGANISM: Clostridium Botulinum
<220> FEATURE:
<223> OTHER INFORMATION: Type F

<400> SEQUENCE: 61

Cys Lys Ser Val Ile Pro Arg Lys Gly Thr Lys Ala Pro Pro Arg Leu
1               5                   10                  15

Cys

<210> SEQ ID NO 62
<211> LENGTH: 15
<212> TYPE: PRT
<213> ORGANISM: Clostridium Botulinum
<220> FEATURE:
<223> OTHER INFORMATION: Type G

<400> SEQUENCE: 62

Cys Lys Pro Val Met Tyr Lys Asn Thr Gly Lys Ser Glu Gln Cys
1               5                   10                  15

<210> SEQ ID NO 63
<211> LENGTH: 29
<212> TYPE: PRT
<213> ORGANISM: Clostridium Tetani
<220> FEATURE:

<400> SEQUENCE: 63

Cys Lys Lys Ile Ile Pro Pro Thr Asn Ile Arg Glu Asn Leu Tyr Asn
1               5                   10                  15

Arg Thr Ala Ser Leu Thr Asp Leu Gly Gly Glu Leu Cys
            20                  25

<210> SEQ ID NO 64
<211> LENGTH: 23
<212> TYPE: PRT
<213> ORGANISM: Influenza A Virus
<220> FEATURE:

<400> SEQUENCE: 64

Gly Leu Phe Gly Ala Ile Ala Gly Phe Ile Glu Asn Gly Trp Glu Gly
1               5                   10                  15

Met Ile Asp Gly Trp Tyr Gly
            20
```